(12) United States Patent
Liu et al.

(10) Patent No.: US 10,441,562 B2
(45) Date of Patent: Oct. 15, 2019

(54) AROMATIC FARNESYL COMPOUND AND APPLICATION THEREOF

(71) Applicant: INSTITUTE OF MICROBIOLOGY, CHINESE ACADEMY OF SCIENCES, Beijing (CN)

(72) Inventors: Hongwei Liu, Beijing (CN); Kai Wang, Beijing (CN); Li Bao, Beijing (CN); Junjie Han, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 15/518,698

(22) PCT Filed: Dec. 18, 2015

(86) PCT No.: PCT/CN2015/097938
§ 371 (c)(1),
(2) Date: Apr. 12, 2017

(87) PCT Pub. No.: WO2016/173274
PCT Pub. Date: Nov. 3, 2016

(65) Prior Publication Data
US 2017/0224651 A1    Aug. 10, 2017

(30) Foreign Application Priority Data

Apr. 30, 2015   (CN) .......................... 2015 1 0217149
Jun. 2, 2015    (CN) .......................... 2015 1 0294277

(Continued)

(51) Int. Cl.
*A61K 31/341*    (2006.01)
*A23L 2/395*     (2006.01)
(Continued)

(52) U.S. Cl.
CPC ............ *A61K 31/341* (2013.01); *A23L 2/395* (2013.01); *A23L 2/40* (2013.01); *A23L 2/52* (2013.01);
(Continued)

(58) Field of Classification Search
CPC .. A61K 31/341; A61K 31/202; A61K 31/365; A61K 31/192; A61K 2300/00;
(Continued)

(56) References Cited

FOREIGN PATENT DOCUMENTS

CN    104496947         4/2015
CN    104496943 A       4/2018
(Continued)

OTHER PUBLICATIONS

Yajima et al (Eur. J. Org. Chem. 2014, 731-738). (Year: 2013).*
(Continued)

*Primary Examiner* — Angela C Brown-Pettigrew
(74) *Attorney, Agent, or Firm* — Stinson LLP

(57) ABSTRACT

Aromatic farnesyl compound and application of a pharmaceutical salt thereof as an inhibitor of α-glucosidase, dipeptidyl peptidase-4, aldose reductase, protein tyrosine phosphatase-1B or HMG-CoA reductase, or use thereof in preparing medicine and functional healthcare products having a liver protective function and/or for treating and/or preventing type II diabetes, diabetic retinopathy, diabetic foot disease, and hyperlipidemia.

16 Claims, 1 Drawing Sheet

(30) Foreign Application Priority Data

| | | | |
|---|---|---|---|
| Jul. 7, 2015 | (CN) | .......................... | 2015 1 0394003 |
| Sep. 11, 2015 | (CN) | .......................... | 2015 1 0578951 |

(51) Int. Cl.

| | |
|---|---|
| *A23L 2/40* | (2006.01) |
| *A23L 2/52* | (2006.01) |
| *A61K 31/192* | (2006.01) |
| *A61K 31/365* | (2006.01) |
| *C07D 307/33* | (2006.01) |
| *C07C 57/03* | (2006.01) |
| *A61K 31/202* | (2006.01) |
| *A23L 33/105* | (2016.01) |

(52) U.S. Cl.
CPC .......... *A23L 33/105* (2016.08); *A61K 31/192* (2013.01); *A61K 31/202* (2013.01); *A61K 31/365* (2013.01); *C07C 57/03* (2013.01); *C07D 307/33* (2013.01); *A61K 2300/00* (2013.01)

(58) Field of Classification Search
CPC .......... A23L 33/105; A23L 2/395; A23L 2/52; A23L 2/40; C07C 57/03; C07D 307/33
See application file for complete search history.

(56) References Cited

FOREIGN PATENT DOCUMENTS

| WO | 00/53207 A1 | 9/2000 |
|---|---|---|
| WO | 2008/108825 A2 | 9/2008 |
| WO | 2018/014660 A1 | 1/2018 |

OTHER PUBLICATIONS

Patani et al (Chem. Rev. 1996, 96, 3147-3176) (Year: 1996).*
Hadigan et al (J Clin Endocrinol Metab 87: 4611-4615, 2002) (Year: 2002).*
Luo, Qi et al., "Isolation and Identification of Renoprotective Substances from the Mushroom Ganoderma Lucidum", Tetrahedron, vol. 71, No. 5, Dec. 20, 2014 (Dec. 20, 2014), ISSN: 0040-4020, pp. 840-845.
Niu, Xuemei et al., "Prenylated Phenolics from Ganoderma Fornicatum", Journal of Natural Products, vol. 69, No. 9, Jul. 15, 2006 (Jul. 15, 2006), ISSN: 0163-3864, pp. 1364-1365.
International Search Report, PCT/CN2015/097938, dated Mar. 23, 2016, 3 pages.
Adams, M., et al., "Antiplasmodial Lanostanes from the Ganoderma lucidum Mushroom," 2010, J Nat Prod, 73:897-900, 4 pages.
Alves, M. J., et al., "Docking Studies in Target Proteins Involved in Antibacterial Action Mechanisms: Extending the Knowledge on Standard Antibiotics to antimicrobial Mushroom Compounds," 2014, Molecules, 19:1672-1684, 13 pages.
Chen, B., et al., "Triterpenes and meroterpenes from Ganoderma lucidum with Inhibitory Activity Agains HMGs Reductase, Aldose Reductase and alpha-Glucosidase," 2017, Fitoterapia, 120:6-16, 11 pages.
El Dine, R. S., et al., "Inhibition of the Dimerization and Active Site of HIV-1 Protease by Secondary Metabolites from the Vietnamese Mushroom Ganoderma colossum," 2009, J Nat Prod, 72:2019-2023, 5 pages.
Peng, X., et al., "Unusual Prenylated Phenols with Antioxidant Activities from Ganoderma cochlear," 2015, 171:251-257, 7 pages.
Wang, K., et al., "A. Novel Class of alpha-Glucosidase and HMB-CoA Reductase Inhibitors from Ganoderma leucocontextum and the Anti-Diabetic Properties of Ganomycin I in KK-Ay Mice," 2017, Euro J Med Chem, 127:1035-1046, 12 pages.

* cited by examiner

AROMATIC FARNESYL COMPOUND AND APPLICATION THEREOF

REFERENCE TO CORRESPONDING APPLICATIONS

The present application is the 371 national stage application based on International Application No. PCT/CN2015/097938, filed Dec. 18, 2015, which claims priority to Chinese Patent Application No. 20151057895.1, filed Sep. 11, 2015, Chinese Patent Application No. 201510394003.2, filed Jul. 7, 2015, Chinese Patent Application No. 201510294277.4, filed Jun. 2, 2015, and Chinese Patent Application No. 201510217149.X, filed Apr. 30, 2015, the entire contents of which are incorporated herein by reference.

FIELD OF TECHNOLOGY

The present invention relates to an application of compounds, specifically relates to an aromatic farnesyl compound and application thereof.

BACKGROUND

With the development of the society, people's living standard is continuously improved and dietary is adjusted. Diet has a trend of surplus growth, which leads to an increase morbidity rate of metabolic diseases. Wherein, most remarkable diseases are hyperglycaemia and hyperlipidemia. Until now, the number of the world's diabetic patients is about 200 million, and the amount is increasing every year with surprising speed. Besides, morbidity rate of atherosclerosis, coronary disease or other angiocardiopathy caused by the rise of blood lipid has increased year by year, and there is a younger trend in the angiocardiopathy. Drugs using in decreasing blood glucose and blood lipid have been one of the important projects in drugs research.

In recent years, successful development of HMG-CoA reductase inhibitors becomes a breakthrough in the studies of lipid-lowering drugs. These drugs, which have good therapeutic effects in treating hypercholesterolemia, can inhibit rate-limiting enzyme (i.e. HMG-CoA reductase) in cholesterol synthesis through competitive inhibition, thus decreasing the level of endogenous cholesterol synthesis.

α-glucosidase, including α-amylase, maltase, isomaltase, sucrase, lactase, trehalase and so on, is a series of hydrolase locating on intestinal villi brush border membrane and mainly participates in body's digestion and absorption of carbohydrate. A-glucosidase inhibitor, a first-line glucose-lowering drug for treating type II diabetics when simply diet control is invalid, can inhibit α-glucosidase on intestinal villi brush border through competitive inhibition or non-competitive inhibition, and delay the process of oligosaccharide or polysaccharide converted into absorbable monosaccharide, thus effectively inhibiting the increase of postprandial blood glucose of diabetics and maintaining blood glucose within the desired range smoothly and slowly.

The main α-glucosidase inhibitors in market include acarbose, voglibose, migltol and so on. It's remarkable that these inhibitors have severe toxic side effects in various degrees, such as gastrointestinal side effects, urticaria, hepatosis and angiocardiopathy risk.

Therefore, it is necessary and urgent to develop a more secure and powerful drug for preventing and treating hyperglycaemia and hyperlipidemia.

Type II occupies the majority in diabetics. Insulin resistance is the key causative factor of type II diabetics and protein tyrosine phosphatase 1B (PTP1B) also plays a key role in the formulation of insulin resistance. Studies have shown that PTP1B, a negative regulator of insulin signal pathway, can dephosphorylate the tyrosine residues both in activated insulin receptors and substrate thereof, thus terminating insulin signal pathway and causing body's insulin resistance and relative insulin deficiency, and finally developing into diabetes type II. Animal research has shown that the insulin sensitivity of PTP1B knockout mouse raises significantly in glucose tolerance and insulin tolerance test. Therefore, PTP1B inhibitor may be considered as a drug which plays an important role in glucose-lowering.

In recent years, as a new direction in treating diabetes, dipeptidyl peptidase-4 (DPP-4) inhibitors have attracted widespread attention of medicinal chemists. In 2006, Merck's sitagliptin has been approved by FDA for marketing as the first DPP-4 inhibitor. Dipeptidyl peptidase-4 (DPP-4) is a kind of serine proteinase which can rapidly cleave and inactivated incretin such as GLP-1 and GIP. As a multipurpose proteolytic enzyme, DPP-4 inhibitors can inhibit the degradation of GLP-1 and GIP, enhance the activity of incretin and neuropeptide, decrease the fasting or postprandial glucose concentration and glycosylated hemoglobin levels, and improve the insulin sensitivity and β cell function.

The hyperfunction of polyols metabolic activity is one of the contributing factors of diabetic complication. With the increase of blood sugar, hexokinase used for catalysing glucose changing into glucose-6-phosphate is saturated, which stimulates the generation of aldose reductase (AR), thus increasing the activity of AR and activate the sorbitol pathway. Due to its polarity, sorbitol is hard to go through the cell membrane. A large amount of sorbitol is produced in cells, which may cause diabetic complication such as diabetic nephropathy, vasculopathy and retinopathy. Aldose reductase inhibitor can inhibit the AR in polyol pathway and prevent the glucose changing into sorbitol, then polyols' level returns to normal, nerve conduct function is improved, and the formation of cataract and the appearance of albuminuria can be delayed, thus achieving the aim of preventing and delaying diabetic complication.

SUMMARY

The present invention provides a series of aromatic farnesyl compounds and pharmaceutically-acceptable salts thereof, which are used as inhibitors of α-glucosidase, dipeptidyl peptidase-4, aldose reductase, protein tyrosine phosphatase 1B or HMG-CoA reductase; or, used in preparing drugs and functional health products for treating and/or preventing diabetes type II and/or hyperlipidemia; or, used in preparing drugs and functional health products having hepatoprotective effect; or, used in preparing drugs and functional health products for treating and/or preventing diabetic retinopathy and diabetic foot.

Inhibitors, drugs and functional health products which are prepared from aromatic farnesyl compound and pharmaceutically-acceptable salts thereof in present invention have significant treatment effect without any side effect.

Therefore, firstly, the present invention provides an application of aromatic farnesyl compounds and pharmaceutically-acceptable salts thereof in any one of the followings:
(1) being used as α-glucosidase inhibitors;
(2) preparing drugs for treating and/or preventing diabetes type II;

(3) preparing drugs for inhibiting α-glucosidase;
(4) being used as HMG-CoA reductase inhibitors;
(5) preparing drugs for treating and/or preventing hyperlipidemia;
(6) preparing drugs for inhibiting HMG-CoA reductase;
(7) preparing foods or functional health products which can decrease hyperglycaemia and hyperlipemia;
(8) being used as protein tyrosine phosphatase 1B inhibitors;
(9) preparing drugs used as protein tyrosine phosphatase 1B inhibitors;
(10) being used as dipeptidyl peptidase-4 inhibitors;
(11) preparing drugs used as dipeptidyl peptidase-4 inhibitors;
(12) being used as aldose reductase inhibitors;
(13) preparing drugs used as aldose reductase inhibitors;
(14) preparing drugs for treating and/or preventing diabetic retinopathy or diabetic foot;
(15) preparing foods or functional health products for treating and/or preventing non-alcohol fatty liver disease.

In the above technical solutions, structure of said aromatic farnesyl compound is represented by formula (I), wherein, $R_1$ is any selected from H, $C_1$-$C_5$ alkyl group, $-NO_2$, F, Cl, Br, ester group, $-OH$, acylamino and alkoxy groups; configuration of 1' is selected from R type and S type; $R_2$ is selected from H and alkoxy groups; X is any selected from O, H, $-OH$ and carbonyl; the bond between 2' and 3' is single bond or double bond; 14' is selected from $-COOH$ and ester group; N=1, 2 or 3; $R_3$ is any selected from $-OH$, $-CHO$, $-COOH$ and ester group.

Formula (I)

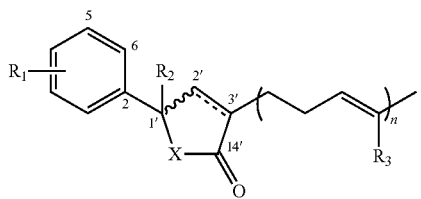

In the above technical solutions, said aromatic farnesyl compound is any selected from S1 to S38 as followings:

S1

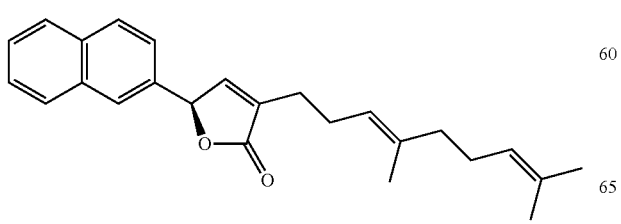

S2

S3

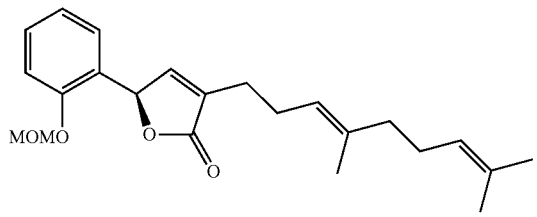

S4

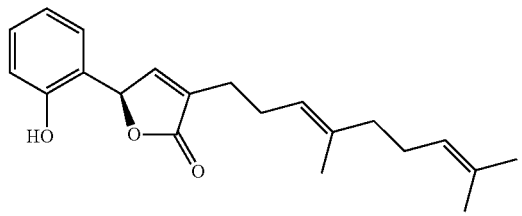

S5

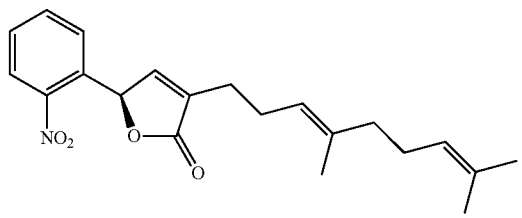

S6

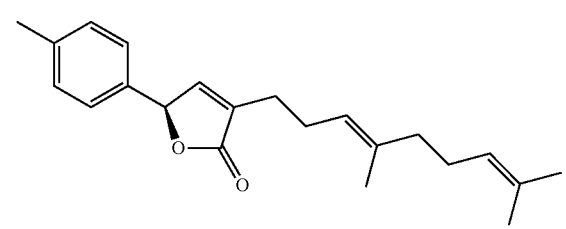

S7

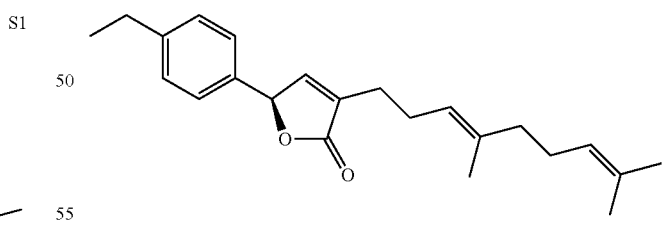

S8

S9
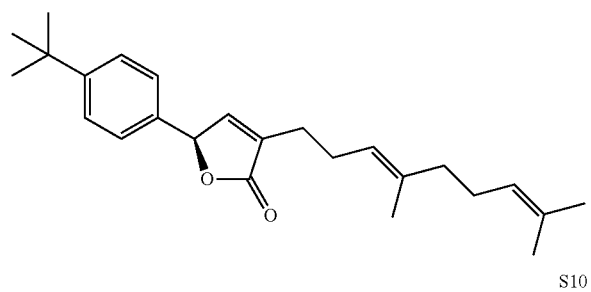
S15
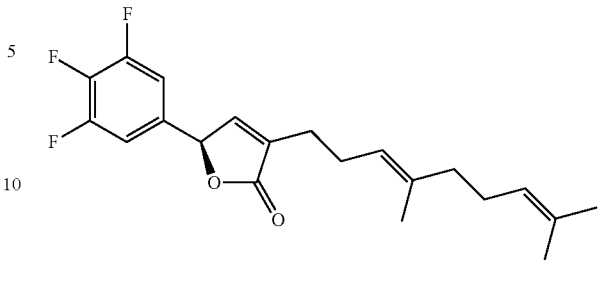
S10
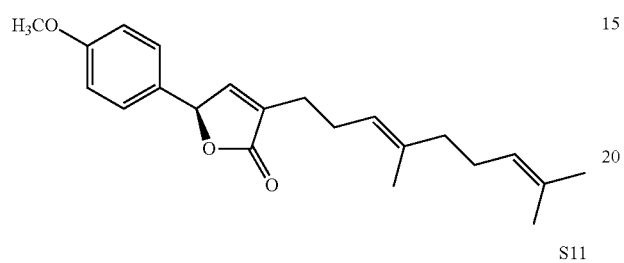
S17
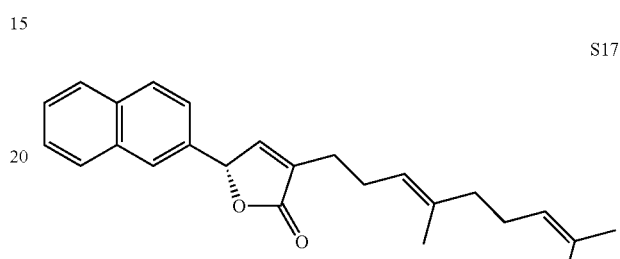
S11
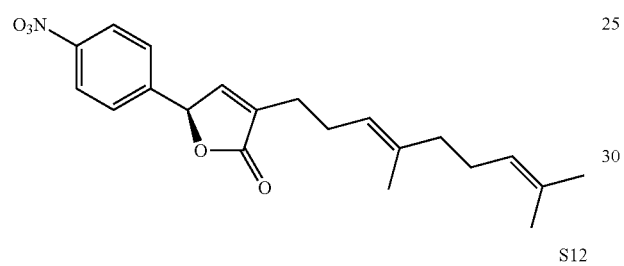
S18
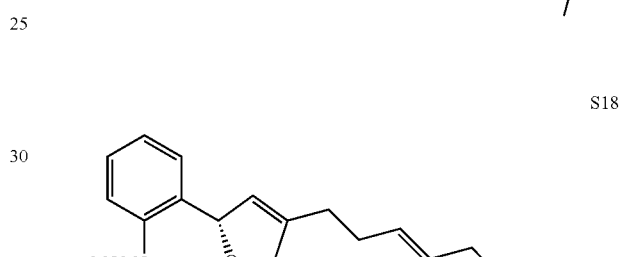
S12
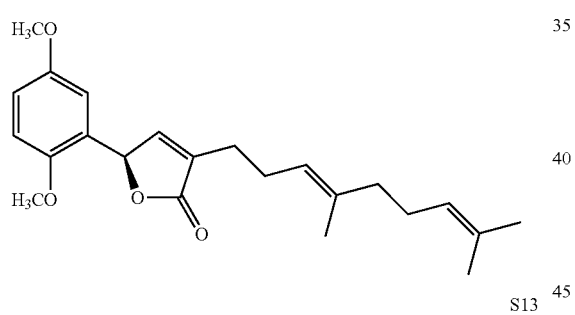
S19
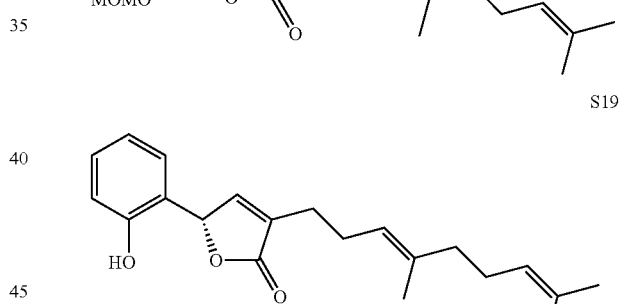
S13
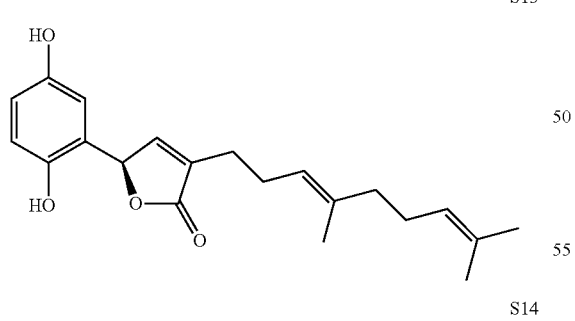
S20
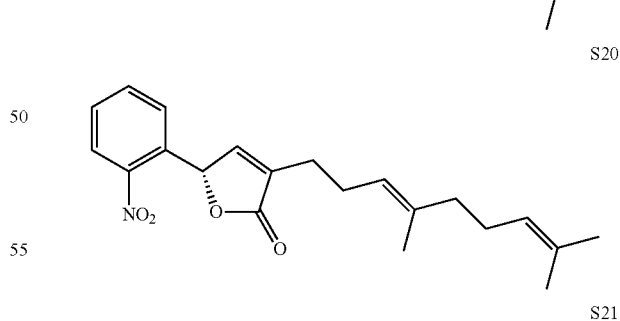
S14
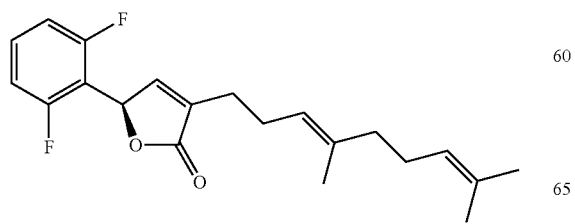
S21
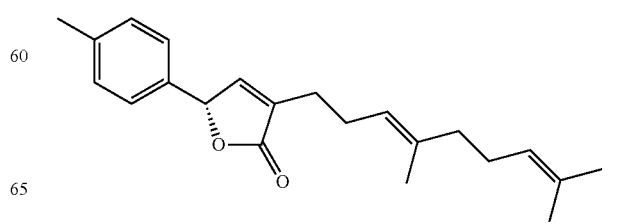

S22
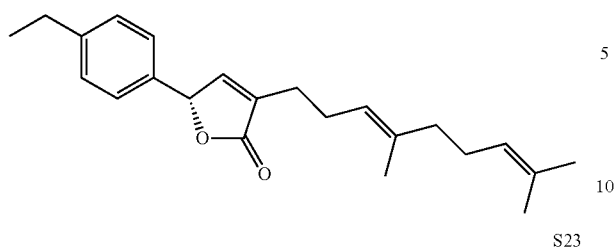
S23
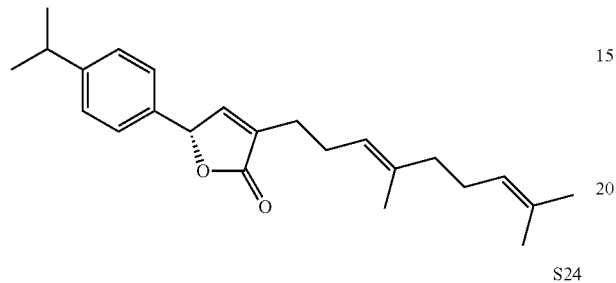
S24
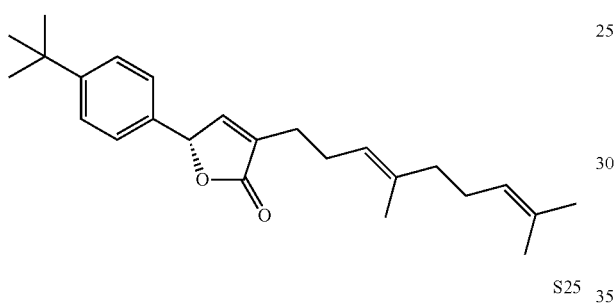
S25
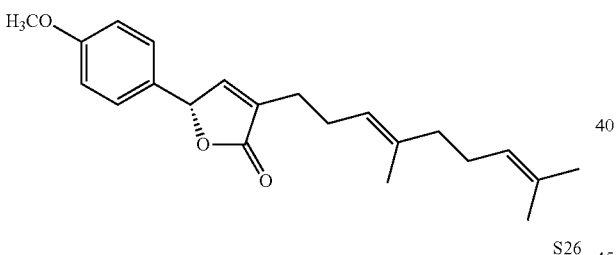
S26
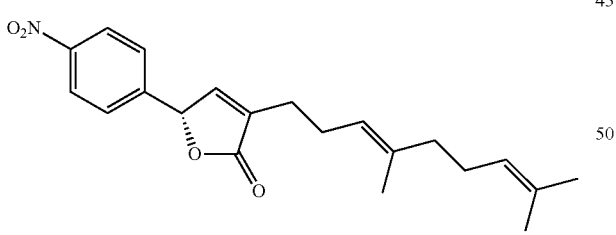
S27
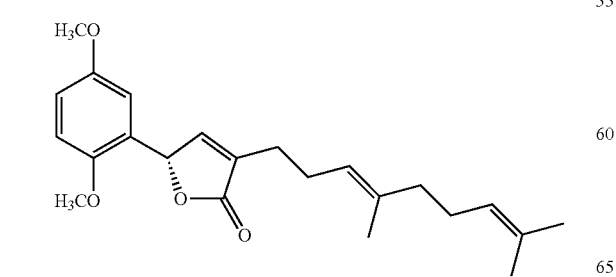
S28
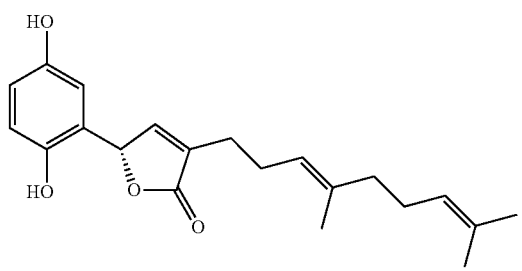
S29
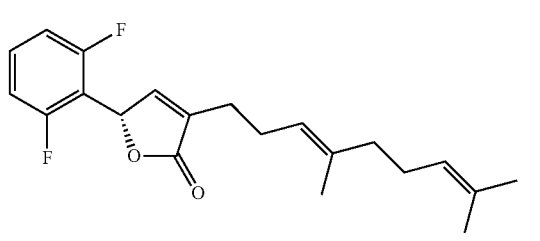
S30
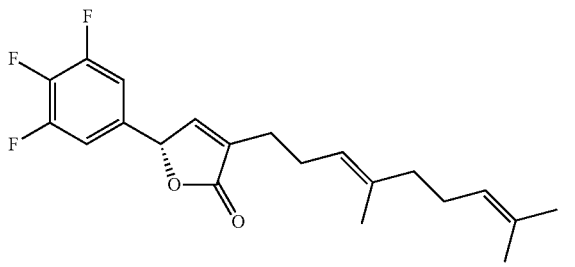
S31
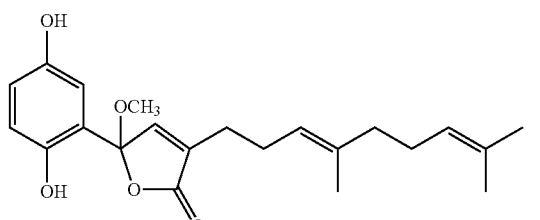
S32
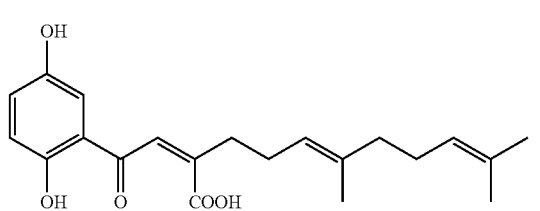
S33
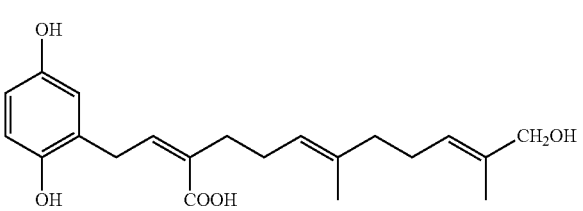

-continued

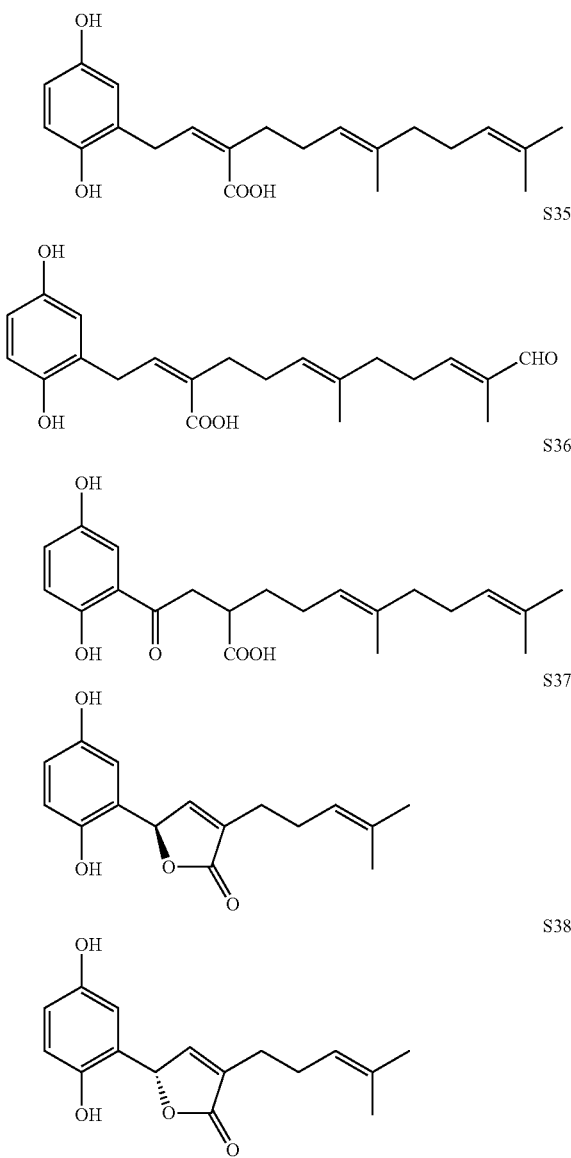

In addition, the present invention provides an application of compositions in any one of the followings, said compositions include at least one of the above compounds and pharmaceutically-acceptable salts thereof represented by formula (I):
(1) being used as α-glucosidase inhibitors;
(2) preparing drugs for treating and/or preventing diabetes type II;
(3) preparing drugs for inhibiting α-glucosidase;
(4) being used as HMG-CoA reductase inhibitors;
(5) preparing drugs for treating and/or preventing hyperlipidemia;
(6) preparing drugs for inhibiting HMG-CoA reductase;
(7) preparing foods or functional health products which can decrease hyperglycaemia and hyperlipemia;
(8) being used as protein tyrosine phosphatase 1B inhibitors;
(9) preparing drugs used as protein tyrosine phosphatase 1B inhibitors;
(10) being used as dipeptidyl peptidase-4 inhibitors;
(11) preparing drugs used as dipeptidyl peptidase-4 inhibitors;
(12) being used as aldose reductase inhibitors;
(13) preparing drugs used as aldose reductase inhibitors;
(14) preparing drugs for treating and/or preventing diabetic retinopathy and diabetic foot;
(15) preparing foods or functional health products for treating and preventing non-alcohol fatty liver disease.

The present invention also provides an aromatic farnesyl compound and pharmaceutically-acceptable salts thereof, said aromatic farnesyl compound is any selected from compounds represented by S1-S12, S14-S27, S29 and S30.

The present invention also provides an application of compositions in preparing hypoglycemic drugs, foods or functional health products, said compositions include at least one of the above compounds represented by formula (I) and metformin.

In the above technical solutions, said inhibitors or drugs are injection, tablet, granule, powder, pill, capsule, oral liquid, ointment, cream or spray.

In the above technical solutions, said foods or functional health products are oral liquid, tea, tablet, capsule, drink or effervescent tablet.

In the above technical solutions, said foods or functional health products are used in daily health care, diabetes prevention or subsidiary action in/after diabetes treatment.

In the above technical solutions, said inhibitors or drugs include one or more pharmaceutically-acceptable excipients.

In the above technical solutions, said excipients include diluent, excipient, filler, adhesive, wetting agent, disintegrating agent, absorption enhancer, surfactant, adsorption carrier, lubricant and sustained-release material.

In the above technical solutions, said drugs are given by oral administration, gastrointestinal administration, injection, spray, physical or chemical mediated administration or being mixed or packaged by other materials.

The aromatic farnesyl compound and pharmaceutically-acceptable salts thereof provided by the present invention can be used as inhibitors of α-glucosidase and HMG-CoA reductase; or, be used in preparing drugs for treating and/or preventing diabetes type II and hyperlipidemia; or, be used in preparing foods or functional health products which can decrease hyperglycaemia and hyperlipemia; or, be used as protein tyrosine phosphatase 1B inhibitors; or, be used in preparing drugs used as protein tyrosine phosphatase 1B inhibitors; or, be used as dipeptidyl peptidase-4 inhibitors; or, be used in preparing drugs used as dipeptidyl peptidase-4 inhibitors; or, be used as aldose reductase inhibitors; or, be used in preparing drugs used as aldose reductase inhibitors.

The experiments have proved that the aromatic farnesyl compound provided by the present invention can effectively inhibit α-glucosidase and dipeptidyl peptidase-4, thus inhibiting the increase of blood glucose; inhibit aldose reductase, thus preventing and delaying diabetic complication; inhibit HMG-CoA reductase, thus decreasing the level of endogenous cholesterol synthesized in body and blood lipid, and inhibiting the occurrence of non-alcohol fatty liver disease; inhibit protein tyrosine phosphatase 1B, maintain the level of body's polyols levels, improve nerve conduct function, delay the formation of cataract and the appearance of albuminuria, thus preventing and delaying diabetic complication. In conclusion, the aromatic farnesyl compound and pharmaceutically-acceptable salts thereof provided by the present invention can be used in treating and preventing diabetes type II and complication thereof by decreasing blood glucose, inhibiting factors caused by insulin resistance symptoms, such as hyperglycemia, hypercholesterolemia and non alcohol fatty liver disease.

DETAILED DESCRIPTION

Figure 1:
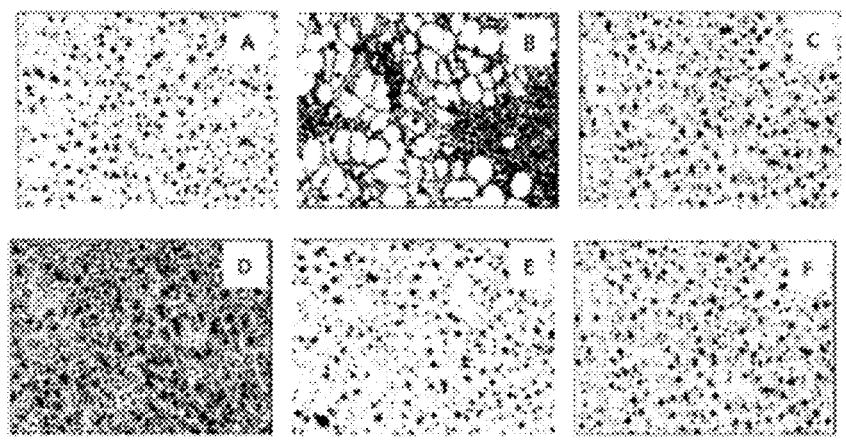
FIG. 1 shows the effects of the compounds S13 and S18 on the liver tissue section of hyperglycemia KK-A$^y$ mice (HE: 20×), wherein, A: normal control group; B: model group; C: compound S13 (10 mg/kg); D: compound S13 (20 mg/kg); E: compound S28 (10 mg/kg); F: compound S28 (20 mg/kg).
Figure 2:
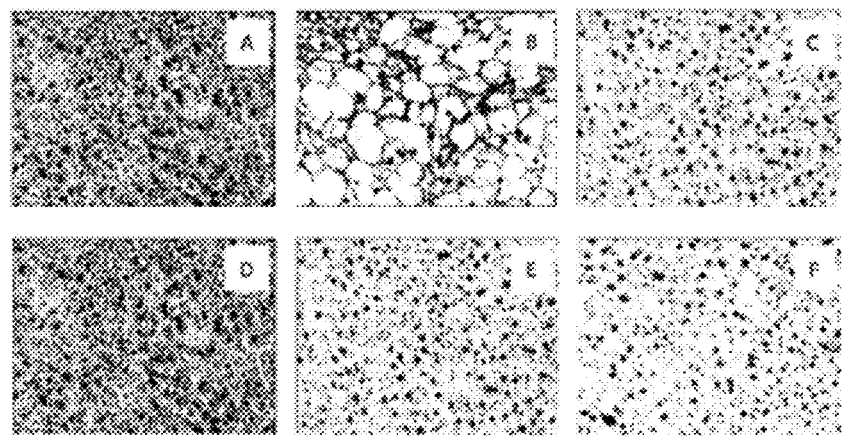
FIG. 2 shows the liver tissue section micrograph (HE: 20×) of Wister rats after administration for 24 days with compounds S13 and S28, wherein, A: normal control group; B: model group C: compound S13 (10 mg/kg); D: compound S13 (20 mg/kg); E: compound S28 (10 mg/kg); F: compound S28 (20 mg/kg).

Examples are provided to describe the present invention in detail below, while the scope of the present invention should not be limited to any of them.

The experiment methods used in the following examples are all conventional methods unless special statements.

The materials and reagents used in the following examples are all commercial available unless special statements.

*Ganoderma lucidum* is purchased from Beijing Tongrentang Pharmacy. α-glucosidase is purchased from Sigma Corporation (Art. No. is G5003); HMG-CoA is purchased from Sigma Corporation (Art. No. is 24895729); NADPH is purchased from Sigma Corporation (Art. No. is 10107824001); 4-nitrophenyl-α-D-glucopyranoside is purchased from J&K Scientific LTD. (Art. No. is 270305); Glucose assay kit is purchased from APPLYGEN Gene Technology Co., Ltd. (Art. No. is E1010); and treptozocin is purchased from J&K Scientific LTD. (Art. No. is M02540). Wistar male rats (SPF) are purchased from Beijing Vital River Laboratory Animal Technology Co., Ltd. All of the synthesized reagents are conventional reagents and purchased from J&K Scientific LTD.

Example 1, Preparation of Compounds S13, S28 and S31-S38

(1) Preparation of Extract from *Ganoderma Lucidum*

*Ganoderma lucidum* is shredded and weighed out at 5 kg, then reflux extracted by 15 L ethanol-water solution, volume percent is 95%, for 3 times, 1 h each time. The extracted solutions are blended and concentrated under vacuum, and 170 g extract is obtained after drying.

The extract is further dissolved in 600 ml distilled water, then extracted for 3 times with equal volume n-hexane. The organic phase is discarded, and the water phase is extracted for 3 times with equal volume acetic ether, then water phase is discarded and the ethyl acetate extract solutions is blended. The ethyl acetate is dried by rotavapor (RE-52AA, purchased from Shanghai YaRong biochemical instrument factory), and then 54 g extract, recorded as LZ-E, is obtained.

(2) Preparation of Compounds

LZ-E, prepared from step (1), is isolated by silica gel column chromatography. System of N-hexane and ethyl acetate, volume ratios of n-hexane and ethyl acetate are 9:1, 4:1, 7:3, 1:1 respectively, is used in gradient elution, 3 retention volumes are used in each gradient elution and each retention volume is 500 ml. According to the thin layer chromatography analysis, distillate LZ-E1 is obtained when the volume ratio of n-hexane and ethyl acetate is 9:1; distillates LZ-E2 to LZ-E3 are obtained when the volume ratio of n-hexane and ethyl acetate is 4:1; distillates LZ-E4 and LZ-E5 are obtained when the volume ratio of n-hexane and ethyl acetate is 7:3; distillate LZ-E6 is obtained when the volume ratio of n-hexane and ethyl acetate volume ratio is 1:1. The above 6 distillates are freeze-dried.

Analysis of the thin layer chromatography has shown that contents of active substances in LZ-E4 are relatively high, thus the distillate LZ-E4 is further isolated by ODS reversed phase silica gel column. Methanol-water solutions with volume concentration of 10%, 20%, 30%, 40%, 50%, 70%, 90% are successively used in elution, 3 retention volumes are used in each elution system and each retention volume is 500 ml. According to the thin layer chromatography analysis, different distillates are identified by 254 nm UV lamp, distillate LZ-E4-1 is obtained in 10% methanol-water solution; distillates LZ-E4-2 to LZ-E4-4 are obtained in 20% methanol-water solution; distillates LZ-E4-5 to LZ-E4-10 are obtained in 30% methanol-water solution; distillates LZ-E4-11 to LZ-E4-14 are obtained in 40% methanol-water solution; distillate LZ-E4-15~LZ-E4-18 are obtained in 50% methanol-water solution; distillates LZ-E4-19 to LZ-E4-23 are obtained in 70% and 90% methanol-water solution. The above 23 distillates are freeze-dried.

Analysis of the thin layer chromatography has shown that contents of active substances in LZ-E4-12 are relatively high, thus the distillate LZ-E4-12 is further isolated by HPLC. Acetonitrile acid water solution with 56% volume concentration, wherein the acid water is water solution of trifluoroacetic acid with 0.01% volume concentration, is used in elution for HPLC preparation, and the flow rate is 2 ml/min Liquid components at chromatographic peaks 18.9, 21.2, 24.5, 26.2, 30.2 and 35.8 min are collected, and compounds S31, S32, S33, S34, S35 and S36 are obtained.

Analysis of the thin layer chromatography has shown that contents of active substances in LZ-E4-14 are relatively high, thus the distillate LZ-E4-14 is further isolated by HPLC. Acetonitrile acid water solution with 52% volume concentration, wherein acid water is water solution of trifluoroacetic acid with 0.01% volume concentration, is used in elution for HPLC preparation, and the flow rate is 2 ml/min Liquid component at chromatographic peaks 22.1 min is collected, and LZ-E4-14-1 is obtained. The LZ-E4-14-1 is separated chirally by HPLC with 45% acetonitrile, and the flow rate is 2 ml/min. Liquid components of chromatographic peaks 31.1 min and 32.5 min are collected, and compounds S13 and S28 are obtained.

Analysis of the thin layer chromatography has shown that contents of active substances in LZ-E4-18 are relatively high, thus the distillate LZ-E4-18 is further isolated by HPLC. Acetonitrile acid water solution with 46% volume concentration, wherein acid water is water solution of trifluoroacetic acid with 0.01% volume concentration, is used in elution for HPLC preparation, and the flow rate is 2 ml/min. Liquid component of chromatographic peaks 15.4 min is collected, and LZ-E4-18-1 is obtained. The LZ-E4-18-1 is separated chirally by HPLC with 40% acetonitrile, and the flow rate is 2 ml/min. Liquid components of chromatographic peaks 25.1 min and 26.4 min are collected, and compounds S37 and S38 are obtained.

Conditions of the above thin layer chromatography are as followings: thin layer plate: Qingdao Haiyang thin layer plate company; thin layer system: chloroform:methanol=20: 1, 2 ml; T (temperature)=25.

Conditions of the above HPLC are as followings: 10 mg/ml sample solution is prepared with methanol of chromatographic pure, injection volume is 15 μL each time, chromatographic column is Kromasil 10×250 mm C18 semi-preparative column, column temperature is 25 and detection wavelength is 210 nm.

Example 2, Synthesis of Compounds S1-S30
Synthetic Route:
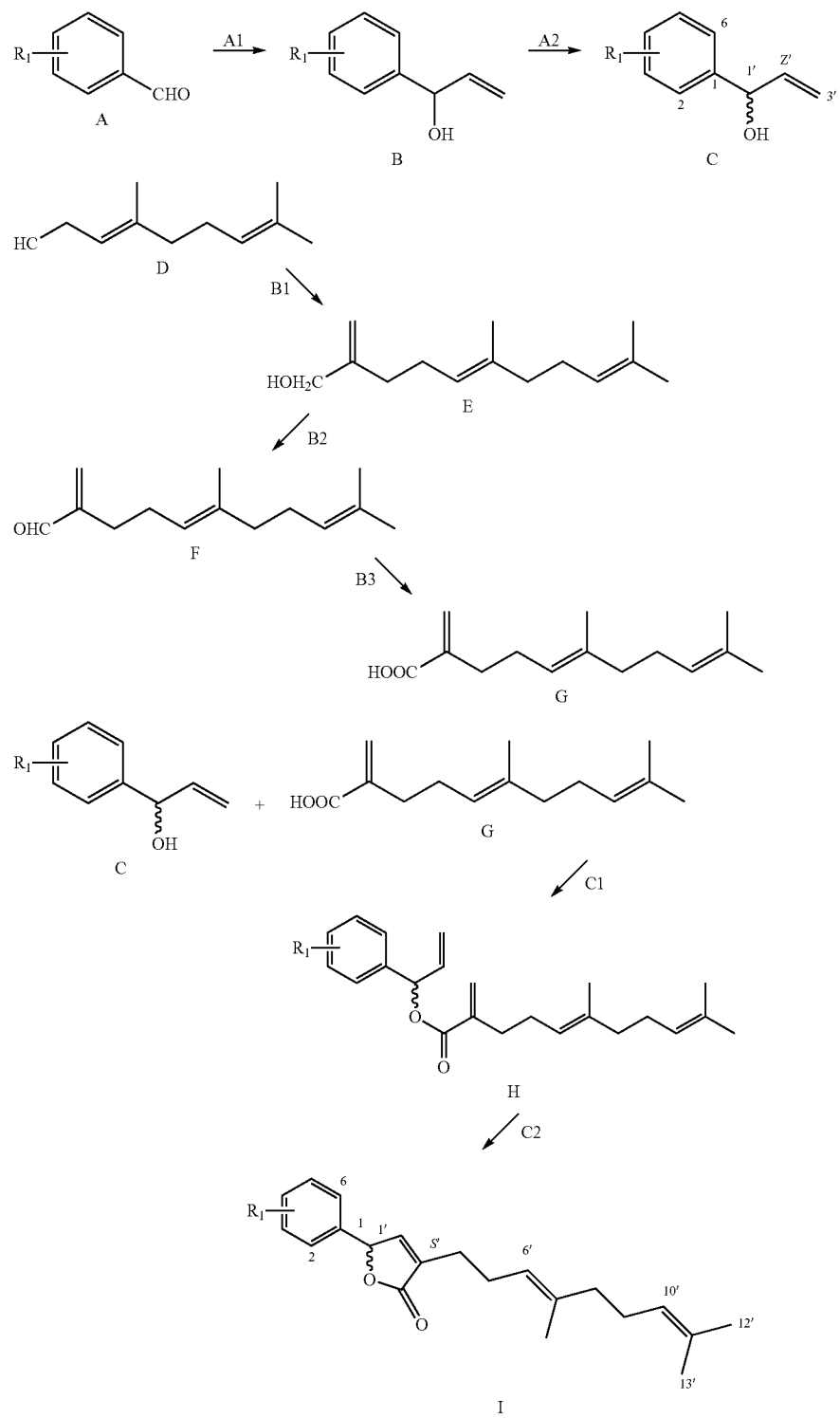

Compound A is selected from benzaldehyde derivatives with different substituents, and the specific structural formulas are shown in the following table:

TABLE 1

The specific structural formulas of benzaldehyde derivatives

| compound | Structural formula |
|---|---|
| A1 | benzaldehyde |
| A2 | 2-naphthaldehyde |
| A3 | 2-(methoxymethoxy)benzaldehyde (OMOM) |
| A4 | 2-nitrobenzaldehyde (NO$_2$) |
| A5 | 4-methylbenzaldehyde |
| A6 | 4-ethylbenzaldehyde |
| A7 | 4-isopropylbenzaldehyde |
| A8 | 4-tert-butylbenzaldehyde |
| A9 | 4-methoxybenzaldehyde (H$_3$CO) |
| A10 | 4-nitrobenzaldehyde (O$_2$N) |
| A11 | 3,4-dimethoxybenzaldehyde (H$_3$CO, OCH$_3$) |

TABLE 1-continued

The specific structural formulas of benzaldehyde derivatives

| compound | Structural formula |
|---|---|
| A12 | 2,6-difluorobenzaldehyde (F, F) |
| A13 | 3,4,5-trifluorobenzaldehyde (F, F, F) |

Compound B: add Vinylmagnesium bromide (1M THF solution, 16 ml, 16 mmol) into −78 anhydrous THF (15 ml) solution of compound A (15.0 mmol) dropwise and stir for 1 h. After being diluted with saturated ammonium chloride (20 ml), the mixed solution is extracted for 3 times with ethyl acetate (30 ml). The organic layers are mixed and then extracted with water and salt water, finally dried by sodium sulfate. After vacuum concentration, the extract is isolated by silica gel column chromatography (n-hexane/ethyl acetate, 10:1), and compound B is obtained.

Compound 1′R-C: add diatomite (3 g) into anhydrous dichloromethane (30 ml) solution of compound B (10.0 mmol) and stir for 5 min. Then add PCC (pyridinium chlorochromate onium salt, 2.56 g) and stir for 3 h. After vacuum concentration, the extract is isolated by fast silica gel column chromatography (n-hexane/ethyl acetate, 10:1), and generated ketone is obtained. Then, the generated ketone is dissolved in 5 ml THF solution and added into toluene solution of (R)-methyl-CBS oxazaborolidine catalyst (1.0 mol/L, 1 mmol, 1 mL) and methyl sulfide solution containing borane (10 mol/L, 1 mmol, 1 mL) at room temperature. Reaction mixture is stirred for 5 h at room temperature. After being added saturated ammonium chloride (10 ml), the mixture is extracted with aether (3×20 mL) and washed by saturated salt solution (2×10 mL), then dried by MgSO$_4$ and evaporate to remove the solvent. The crude product is isolated by fast silica gel column chromatography (n-hexane/ethyl acetate, 10:1) and compound 1′R-C is obtained.

Compound 1′S-C: add diatomite (3 g) into anhydrous dichloromethane (30 ml) solution containing B (10.0 mmol) and stir for 5 min. Then add PCC (pyridinium chlorochromate onium salt, 2.56 g) and stir for 3 h. After vacuum concentration, the extract is isolated by fast silica gel column chromatography. Then, the generated ketone is dissolved in 5 ml THF (tetrahydrofuran) solution and add the solution into toluene solution of (S)-methyl-CBS oxazaborolidine catalyst (1.0 mol/L, 1 mmol, 1 mL) and methyl sulfide solution of borane (10 mol/L, 1 mmol, 1 mL) at room temperature. Reaction mixture is stirred for 5 h at room temperature. After being added saturated ammonium chloride (10 ml), the mixture is extracted with aether (3×20 mL) and washed by saturated salt solution (2×10 mL), then dried by MgSO$_4$ and evaporated to remove the solvent. The crude product is isolated by fast silica gel column chromatography (n-hexane/ethyl acetate, 10:1) and compound 1′S-C is obtained.

(E)-6,10-dimethyl-2-Methyleneundeca-5,9-dien-1-ol (E): add triphenylphosphine (10.2 g, 38.9 mmol) into carbon tetrachloride solution (50 ml) of geraniol (4 g, 32.4 mmol). The reaction mixture is heated to reflux for 1 h, then cooled to 0. After adding 20 ml n-hexane solution, the mixture is stirred for 5 min After being filtrated, the filter liquor is concentrated under vacuum and geraniol chloride is obtained.

Add n-Butyl lithium (2.86M n-hexane solution, 48.5 ml, 130 mmol) into −78 tetramethylethylenediamine solution (TMEDA, 19.5 ml, 130 mmol) dropwise to produce a white precipitate, and stir for 10 min, then add 2-methallyl alcohol (6.82 ml, 81.0 mmol) and anhydrous ether (80 ml) dropwise into the reaction system. The reaction mixture is stirred for 22 h at room temperature. When dark orange jelly appears in the system, cool the system to −78 and add 10 ml aether solution of geraniol chloride. Then the reaction system is stirred for 1 h at room temperature. After being cooled to 0 and diluted with 1N HCl (100 ml), the mixture is extracted with aether (200 ml) for 3 times. Organic layer is mixed and then extracted with water and salt water, finally dried by sodium sulfate. After vacuum concentration, the extract is isolated by silica gel column chromatography (n-hexane/ethyl acetate, 10:1) and colorless oil (E)-6,10-dimethyl-2-Methyleneundeca-5,9-dien-1-ol (E) (4.81 mg, 90%) is obtained.

(E)-6,10-dimethyl-2-Methyleneundeca-5,9-dienal (F): add activated manganese bioxide (14.4 g, 162 mmol) into n-hexane solution (10 ml) of (E)-6,10-dimethyl-2-Methylene-5,9-undecadiene-1-ol (E) (3.95 g, 90%). The reaction system is stirred for 6 h at room temperature. After filtration and vacuum concentration, the extract is isolated by silica gel column chromatography (n-hexane/ethyl acetate, 10:1) and colorless oil (E)-6,10-dimethyl-2-Methyleneundeca-5,9-dienal (F) (5.01 g, 75%) is obtained.

(E)-6,10-dimethyl-2-Methyleneundeca-5,9-dienoic acid (G): add sodium dihydrogen phosphate (2.54 g, 20.9 mmol) solution (5 ml) and sodium hypochlorite (80%, 1.14 g, 12.4 mmol) into 0 mixture of (E)-6,10-dimethyl-2-Methylene-5,9-undecadiene-1-carboxaldehyde (F) (850 mg, 4.12 mmol), tert-butyl alcohol (20 ml) of 2-methyl-2-butene (4.90 ml, 41.2 mmol) and water (10 ml). The reaction system is stirred for 1 h at room temperature. After being diluted with salt solution (30 ml) and extracted with dichloromethane (30 ml) for 3 times, organic layer is mixed and then extracted with water and salt water, finally dried by sodium sulfate. After vacuum concentration, the extract is isolated by silica gel column chromatography (n-hexane/ethyl acetate, 10:1) and colorless oil (E)-6,10-dimethyl-2-Methylene-5,9-undecadiene-1-carboxylic acid (G) (760 mg, 83%) is obtained.

Compound 1'R-H: add diisopropylamine (110 μL, 631 μmol), 2,4,6-Trichlorobenzoyl chloride (100 μL, 631 μmol) and 4-dimethylamino Pyridine (154 mg, 1.26 mmol) into 0 toluene solution of (E)-6,10-dimethyl-2-Methyleneundeca-5,9-dienoic acid (G) (35.1 mg, 158 μmol). Then add toluene solution of 1'R-C (40.1 mg, 124 μmol) and dilute the reaction mixture with 2 ml toluene solution. The reaction system is stirred for 8 h at room temperature. After being diluted with saturated sodium bicarbonate solution (15 ml) of benzene (10 ml) and extracted with ethyl acetate (30 ml) for 3 times, organic layer is mixed and then extracted with water and salt water, finally dried by sodium sulfate. After vacuum concentration, the extract is isolated by silica gel column chromatography (n-hexane/ethyl acetate, 10:1) and colorless oil (1'R, 5E)-1'-[2", 5"-di(methoxyl methoxyl) benzene]prop-2-ene-1-yl-6,10-dimethyl-2-Methyleneundeca-5,9-dienoate (H) (67.0 mg, 92%) is obtained.

Compound 1'S-H: add diisopropylamine (110 μL, 631 μmol), 2,4,6-Trichlorobenzoyl chloride (100 μL, 631 μmol) and 4-dimethylamino Pyridine (154 mg, 1.26 mmol) into 0° C. toluene solution of (E)-6,10-dimethyl-2-Methylene-5,9-undecadiene-1-carboxylic acid (G) (35.1 mg, 158 μmol). Then add toluene solution of 1'S-C (40.1 mg, 124 μmol) and dilute the reaction mixture with 2 ml toluene solution. The reaction system is stirred for 8 h at room temperature. After being diluted with saturated sodium bicarbonate solution (15 ml) of benzene (10 ml) and extracted with ethyl acetate (30 ml) for 3 times, organic layer is mixed and then extracted with water and salt water, finally dried by sodium sulfate. After vacuum concentration, the extract is isolated by silica gel column chromatography (n-hexane/ethyl acetate, 10:1) and colorless oil 1'S-H (69.0 mg, 93%) is obtained.

Compound 1'R-I (S1-S15): degassed dichloromethane solution (2 ml) of 1'R-H (15.1 mg, 32.9 μmol) and Grubbs 1 generation catalyst (1.4 mg, 1.6 μmol) is stirred for 5 h at room temperature. Then add Grubbs 1 generation catalyst (1.4 mg, 1.6 μmol) again and stir for 3 h. After vacuum concentration, the extract is isolated by silica gel column chromatography (n-hexane/ethyl acetate, 10:1) and colorless oil 1'R-I (11.0 mg, 80%) is obtained.

Compound 1'S-I (S16-S30): degassed dichloromethane solution (2 ml) of 1'S-H (15.1 mg, 32.9 μmol) and Grubbs 1 generation catalyst (1.4 mg, 1.6 μmol) is stirred for 5 h at room temperature. Then add Grubbs 1 generation catalyst (1.4 mg, 1.6 μmol) again and stir for 3 h. After vacuum concentration, the extract is isolated by silica gel column chromatography (n-hexane/ethyl acetate, 10:1) and colorless oil 1'S-I (11.0 mg, 80%) is obtained.

Example 3, Compounds S1-S38

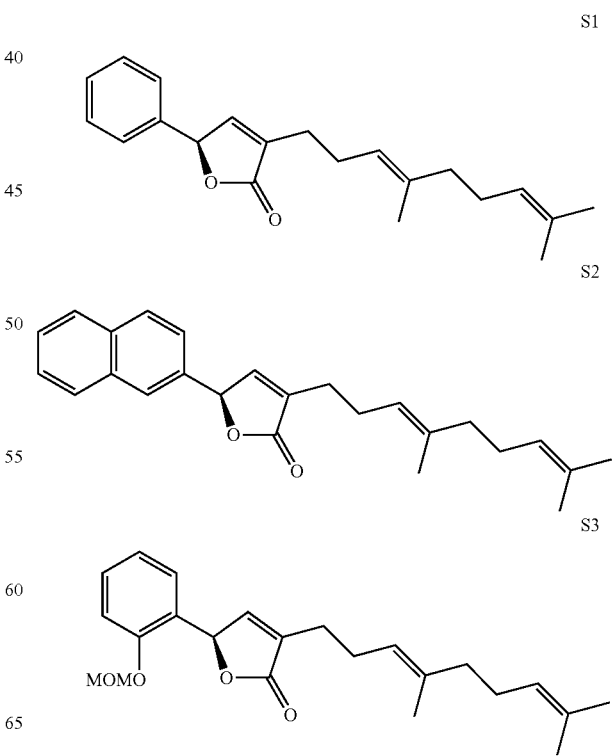

-continued
S4
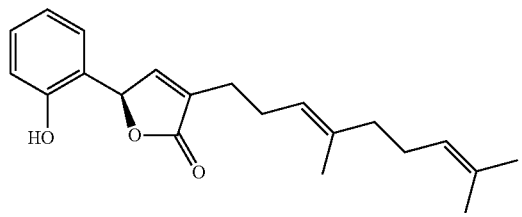
S5
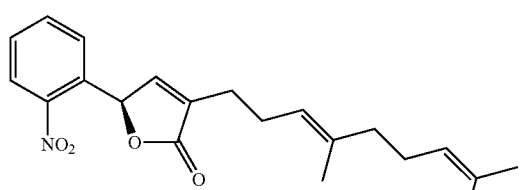
S6
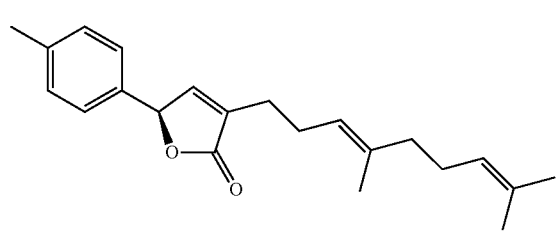
S7
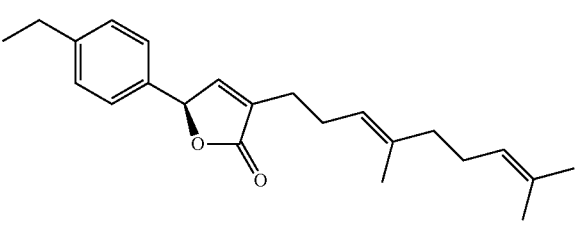
S8
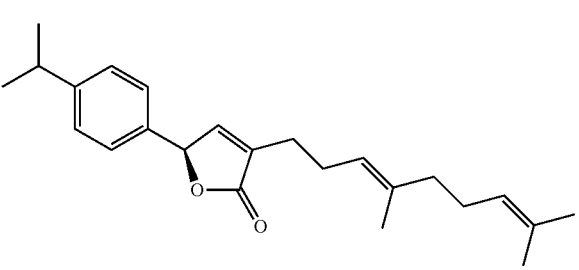
S9
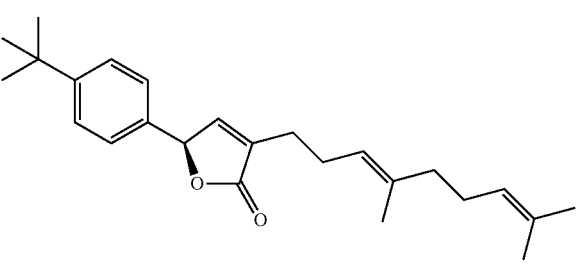
-continued
S10
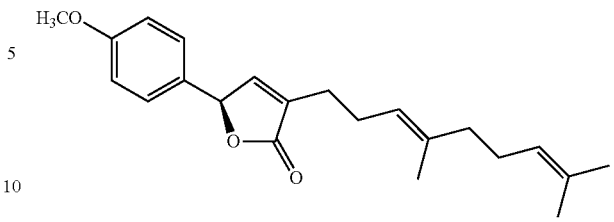
S11
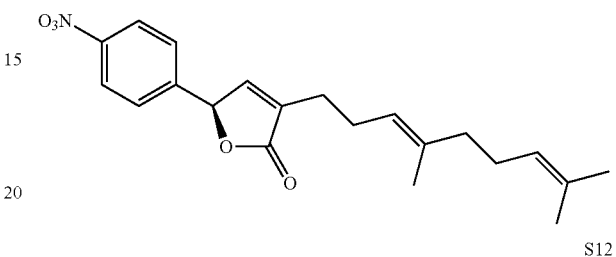
S12
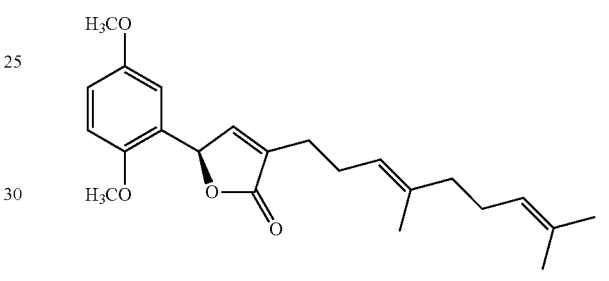
S13
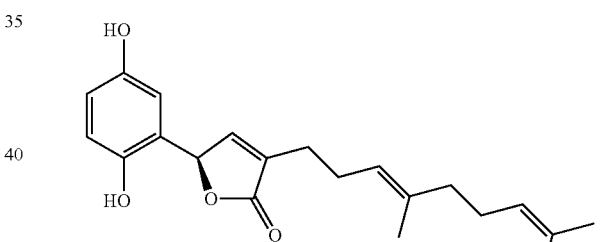
S14
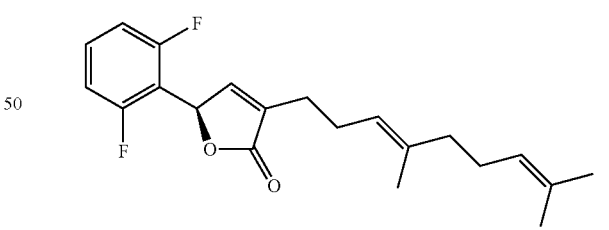
S15
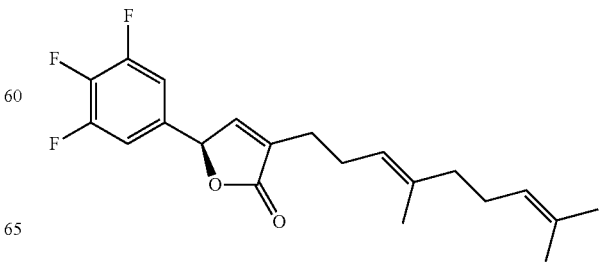

S17
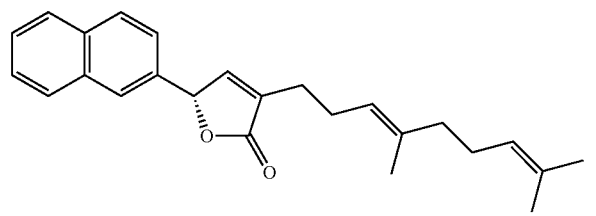
S18
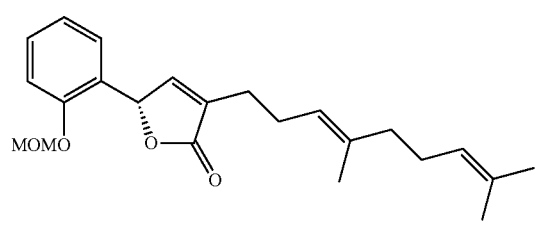
S19
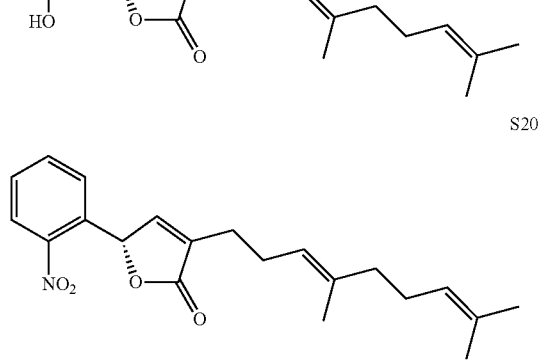
S20
S21
S22
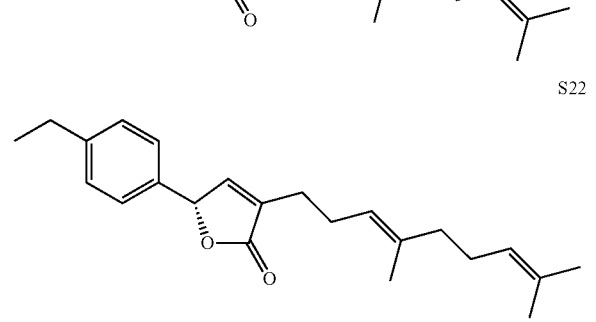
S23
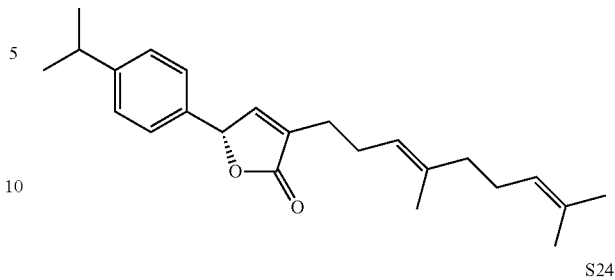
S24
S25
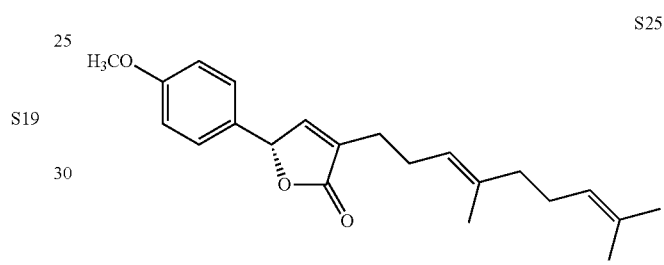
S26
S27
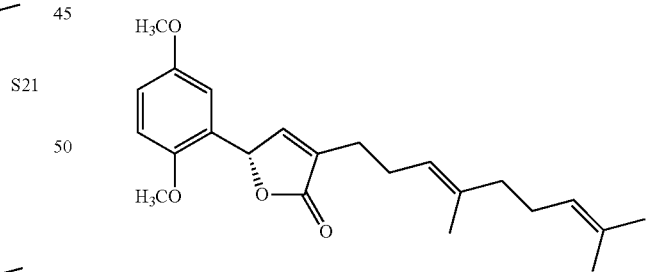
S28
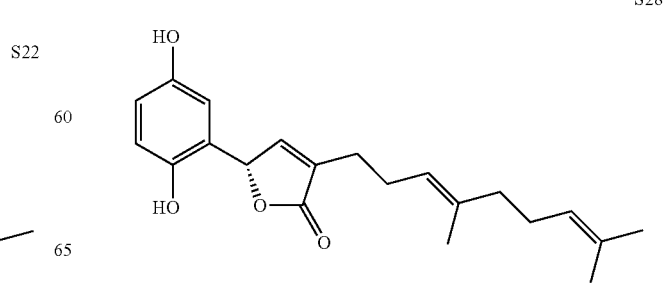

-continued

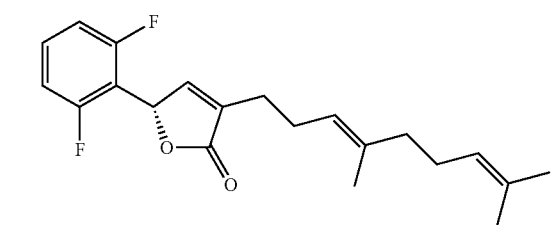
S29

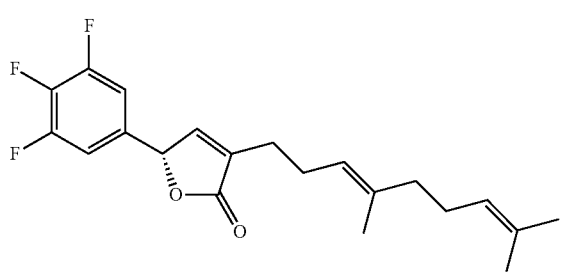
S30

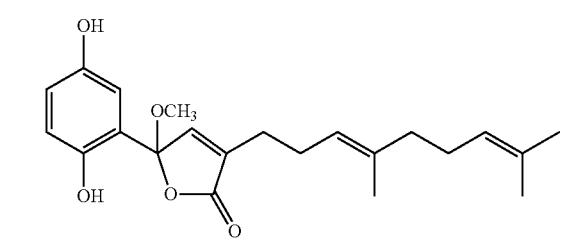
S31

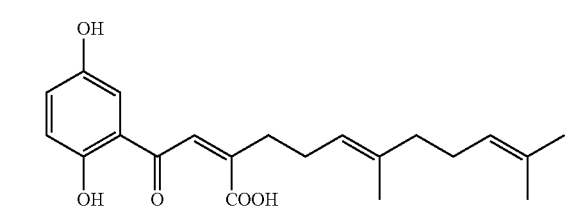
S32

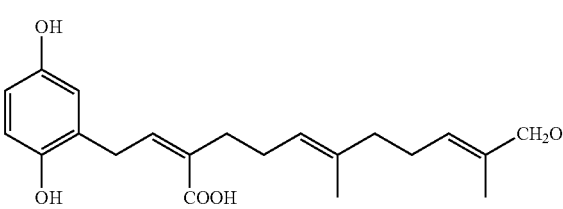
S33

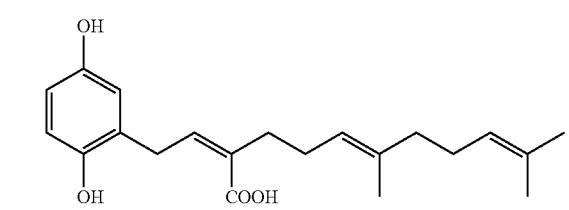
S34

-continued

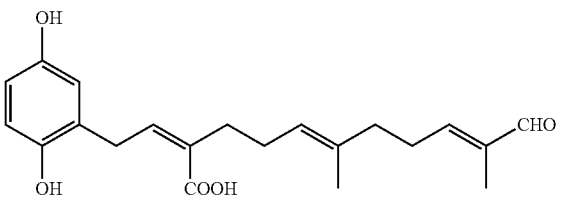
S35

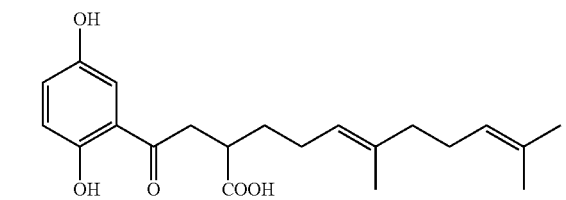
S36

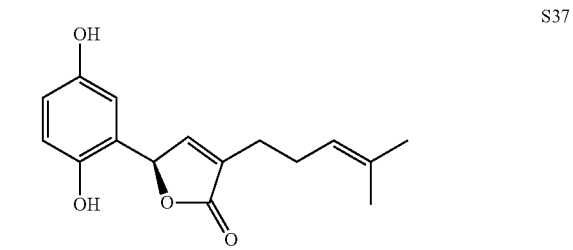
S37

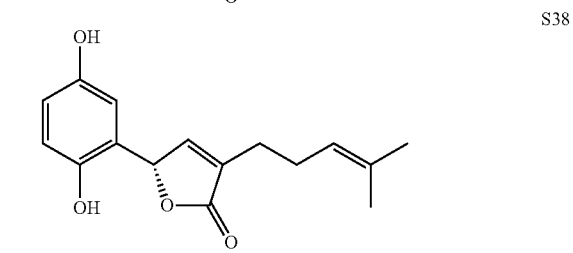
S38

The molecular structures of the above compounds are detected by nuclear magnetic resonance, infrared detection and mass-spectrometric detection.

Wherein, the NMR spectrometers used in determination are BrukerMercury-500 and BrukerMercury-500 MHz (Bruker Optics Instruments Corporation), infrared spectrometer is Nicolet IS5FT-IR (Thermo Nicolet Corporation), and mass spectrometer is Bruker APEX III 7.0T and APEX II FT-ICR (Bruker Optics Instruments Corporation).

S1, (R,E)-3-(4,8-dimethylnona-3,7-dien-1-yl)-5-phenyl-furan-2 (5H)-one, yellow oil, $[\alpha]_D^{25}$+51.0 (c 0.1, MeOH); $^1$H NMR (CDCl$_3$, 500 MHz): δH; 7.33 (t, 8.3, 2H), 7.27 (t, 8.3, 1H), 7.24 (s, 1H), 7.15 (d, 8.3, 2H), 6.43 (s, 1H), 5.09 (t, 7.0, 1H), 5.06 (t, 7.0, 1H), 2.39 (t, 7.0, 2H), 2.33 (m, 2H), 2.02 (m, 2H), 1.96 (m, 2H), 1.66 (s, 3H), 1.58 (s, 6H); $^{13}$C NMR (CDCl$_3$, 125 MHz): δC: 174.0, 147.1, 141.5, 136.8, 133.2, 131.5, 128.9 (×2), 127.5 (×2), 127.1, 124.1, 122.2, 82.1, 39.6, 26.8, 25.7, 25.4, 21.2, 17.8, 16.2; positive HRTOFMS m/z [M+H]$^+$311.2009 (calculated value C$_{21}$H2$_6$O$_2$, 311.2006).

S2, (R,E)-3-(4,8-dimethylnona-3,7-dien-1-yl)-5-(naphthalen-2-yl)furan-2 (5H-one, yellow oil, $[\alpha]_D^{25}$+17.4 (c 0.1, MeOH); $^1$H NMR (CDCl3, 500 MHz): δH; 8.08 (d, 8.4, 1H), 7.91 (d, 8.0, 1H), 7.86 (d, 8.0, 1H), 7.60 (t, 7.6, 1H), 7.56 (t, 7.6, 1H), 7.44 (t, 7.6, 1H), 7.39 (m, 1H), 7.36 (m, 1H), 6.66 (s, 1H), 5.13 (t, 7.0, 1H), 5.06 (t, 7.0, 1H), 2.43 (t, 7.0, 2H), 2.33 (m, 2H), 2.02 (m, 2H), 1.97 (m, 2H), 1.66 (s, 3H), 1.58 (s, 6H); $^{13}$C NMR (CDCl$_3$, 125 MHz): δC 173.8, 147.4, 136.9, 134.0, 133.8, 131.5, 131.3, 130.7, 129.6, 129.1, 126.9, 126.1, 125.4, 124.1, 123.5, 122.6, 122.5, 79.3, 39.6, 26.6, 25.7, 25.7, 25.5, 17.7, 16.2; positive HRTOFMS m/z [M+H]$^+$361.2162 (calculated value $C_{25}H_{28}O_2$, 361.2162).

S3, (R,E)-3-(4,8-dimethylnona-3,7-dien-1-yl)-5-(2-(methoxymethoxy)phenyl furan-2(5H)-one, yellow oil, $[\alpha]_D^{25}$+71.0 (c 0.1, MeOH); $^1$H NMR (CDCl$_3$, 500 MHz): δH; 7.27 (s, 1H), 7.21 (t, 7.7, 1H), 7.15 (d, 7.5, 1H), 6.93 (t, 7.5, 1H), 6.81 (d, 7.5, 1H), 6.23 (s, 1H), 6.01 (s, 2H), 3.50 (s, 3H), 2.38 (t, 7.5, 2H), 2.29 (m, 2H), 2.03 (m, 2H), 1.96 (m, 2H), 1.67 (s, 3H), 1.59 (s, 3H), 1.58 (s, 3H); $^{13}$C NMR (CDCl3, 125 MHz): δC 174.1, 153.0, 147.1, 136.8, 133.1, 131.5, 129.8, 126.6, 124.2, 122.6, 122.1, 121.3, 115.8, 95.2, 78.0, 50.9, 39.6, 26.5, 25.7, 25.7, 25.4, 17.1, 16.1; positive HRTOFMS m/z [M+H]$^+$371.2221 (calculated value $C_{23}H_{30}O_4$, 371.2217).

S4, (R,E)-3-(4,8-dimethylnona-3,7-dien-1-yl)-5-(2-hydroxyphenyl)furan-2 (5-H)-one, yellow oil, $[\alpha]_D^{25}$+54.2 (c 0.1, MeOH); $^1$H NMR (CDCl$_3$, 500 MHz): δH; 7.27 (s, 1H), 7.21 (t, 7.7, 1H), 7.15 (d, 7.5, 1H), 6.93 (t, 7.5, 1H), 6.81 (d, 7.5, 1H), 6.23 (s, 1H), 2.38 (t, 7.5, 2H), 2.29 (m, 2H), 2.03 (m, 2H), 1.96 (m, 2H), 1.67 (s, 3H), 1.59 (s, 3H), 1.58 (s, 3H); 6H; $^{13}$C NMR (CDCl3, 125 MHz): δC 174.1, 153.0, 147.1, 136.8, 133.1, 131.5, 129.8, 126.6, 124.2, 122.6, 122.1, 121.3, 115.8, 78.0, 39.6, 26.5, 25.7, 25.7, 25.4, 17.1, 16.1; positive HRTOFMS m/z [M+H]$^+$327.1954 (calculated value $C_{21}H_{26}O_3$, 327.1953).

S5, (R,E)-3-(4,8-dimethylnona-3,7-dien-1-yl)-5-(2-nitrophenyl)furan-2(5H)-one, yellow oil, $[\alpha]_D^{25}$+38.2 (c 0.1, MeOH); $^1$H NMR (CDCl$_3$, 500 MHz): δH 8.17 (d, 8.3, 1H), 7.68 (t, 7.6, 1H), 7.54 (d, 7.9, 1H), 7.53 (m, 1H), 7.33 (s, 1H), 6.53 (s, 1H), 5.06 (m, 2H), 2.38 (t, 7.6, 2H), 2.26 (m, 2H), 1, 99 (m, 2H), 1.95 (m, 2H), 1.66 (s, 3H), 1.58 (s, 6H); $^{13}$C NMR (CDCl3, 125 MHz): δC 173.7, 148.1, 147.1, 137.0, 134.7, 133.6, 132.3, 131.5, 129.4, 128.1, 125.3, 124.1, 122.3, 78.4, 39.6, 26.6, 25.7, 25.7, 25.4, 17.7, 16.1; positive HRTOFMS m/z [M+H]$^+$356.1855 (calculated value $C_{21}H_{25}NO_4$, 356.1856).

S6, (R,E)-3-(4,8-dimethylnona-3,7-dien-1-yl)-5-(p-tolyl)furan-2(5H)-one, yellow oil, $[\alpha]_D^{25}$+39.0 (c 0.1, MeOH); $^1$H NMR (CDCl$_3$, 500 MHz): δH; 7.18 (d, 7.9, 2H), 7.13 (d, 7.9, 2H), 7.08 (s, 1H), 5.83 (s, 1H), 5.12 (t, 7.5, 1H), 5.07 (t, 7.5, 1H), 2.40 (m, 2H), 2.35 (s, 3H), 2.31 (m, 2H), 2.04 (m, 2H), 1.98 (m, 2H), 1.67 (s, 3H), 1.59 (s, 3H), 1.58 (s, 3H); $^{13}$C NMR (CDCl$_3$, 125 MHz): δC: 174.0, 147.9, 139.1, 136.8, 133.5, 132.1, 131.5, 129.5 (×2), 126.6 (×2), 124.1, 122.6, 82.2, 39.6, 26.6, 25.7, 25.7, 25.4, 21.2, 17.7, 16.2; positive HRTOFMS m/z [M+H]$^+$325.2166 (calculated value $C_{22}H_{28}O_2$, 325.2162).

S7, (R,E)-3-(4,8-dimethylnona-3,7-dien-1-yl)-5-(4-ethylphenyl)furan-2(5H)-one, yellow oil, $[\alpha]_D^{25}$+54.9 (c 0.1, MeOH); $^1$H NMR (CDCl$_3$, 500 MHz): δH; 7.20 (d, 7.9, 2H), 7.13 (d, 7.9, 2H), 7.06 (s, 1H), 5.84 (s, 1H), 5.12 (t, 7.5, 1H), 5.07 (t, 7.5, 1H), 2.65 (q, 7.6, 2H), 2.41 (m, 2H), 2.32 (m, 2H), 2.05 (m, 2H), 1.98 (m, 2H), 1.67 (s, 3H), 1.59 (s, 3H), 1.58 (s, 3H), 1.23 (t, 7.6, 3H); $^{13}$C NMR (CDCl$_3$, 125 MHz); δC: 174.0, 147.9, 145.4, 136.8, 133.5, 132.4, 131.5, 128.4 (×2), 126.6 (×2), 124.1, 122.6, 82.3, 39.6, 28.6, 26.6, 25.7, 25.7, 25.4, 17.7, 16.2, 15.5; positive HRTOFMS m/z [M+H]$^+$339.2322 (calculated value $C_{23}H_{30}O_2$, 339.2319).

S8, (R,E)-3-(4,8-dimethylnona-3,7-dien-1-yl)-5-(4-isopropylphenyl)furan-2(5H)-one, yellow oil, $[\alpha]_D^{25}$+48.0 (c 0.1, MeOH); $^1$H NMR (CDCl3, 500 MHz): δH; 7.26 (d, 7.9, 2H), 7.19 (d, 7.9, 2H), 7.10 (s, 1H), 5.87 (s, 1H), 5.15 (m, 2H), 5.08 (m, 2H), 2.94 (m, 1H), 2.41 (m, 2H), 2.33 (m, 2H), 2.06 (m, 2H), 2.00 (m, 2H), 1.69 (s, 3H), 1.62 (s, 6H), 1.28 (s, 3H), 1.26 (s, 3H); δC: 174.0, 150.1, 147.9, 136.8, 133.5, 132.5, 131.5, 127.0 (×2), 126.7, 126.6, 124.2, 122.6, 82.2, 39.6, 33.9, 26.6, 25.7, 25.7, 25.4, 23.9 (×2), 17.7, 16.2; positive HRTOFMS m/z [M+H]$^+$ 353.2475 (calculated value $C_{24}H_{32}O_2$, 353.2475).

S9, (R,E)-5-(4-(tert-butyl)phenyl)-3-(4,8-dimethylnona-3,7-dien-1-yl)furan-2 (5H)-one, yellow oil, $[\alpha]_D^{25}$+58.0 (c 0.1, MeOH); $^1$H NMR (CDCl$_3$, 500 MHz): δH: 7.40 (d, 7.6, 2H), 7.18 (d, 7.6, 2H), 7.07 (s, 1H), 5.85 (s, 1H), 5.11 (t, 7.5, 1H), 5.07 (t, 7.5, 1H), 2.40 (m, 2H), 2.31 (m, 2H), 2.05 (m, 2H), 1.98 (m, 2H), 1.67 (s, 3H), 1.59 (s, 6H), 1.31 (s, 9H); $^{13}$C NMR (CDCl$_3$, 125 MHz): δC: 174.0, 152.3, 147.9, 136.8, 133.5, 132.1, 131.5, 126.4 (×2), 125.9 (×2), 124.1, 122.6, 82.2, 39.6, 34.7, 31.2 (×3), 26.6, 25.7, 25.7, 25.4, 17.7, 16.2; positive HRTOFMS m/z [M+H]$^+$367.2632 (calculated value $C_{25}H_{34}O_2$, 367.2632).

S10, (R,E)-3-(4,8-dimethylnona-3,7-dien-1-yl)-5-(4-methoxyphenyl)furan-2(5H)-one, yellow oil, $[\alpha]_D^{25}$+78.0 (c 0.1, MeOH); $^1$H NMR (CDCl$_3$, 500 MHz): δH: 7.17 (d, 7.6, 2H), 7.05 (d, 7.6, 2H), 6.89 (s, 1H), 5.82 (s, 1H), 5.12 (t, 7.5, 1H), 5.07 (t, 7.5, 1H), 3.81 (s, 3H), 2.40 (m, 2H), 2.32 (m, 2H), 2.04 (m, 2H), 1.99 (m, 2H), 1.67 (s, 3H), 1.59 (s, 6H); $^{13}$C NMR (CDCl$_3$, 125 MHz) δC: 174.0, 160.3, 147.8, 136.8, 133.7, 131.5, 128.2 (×2), 127.0, 124.1, 122.6, 114.3 (×2), 82.1, 55.4, 39.7, 26.6, 25.7, 25.7, 25.4, 17.7, 16.2; positive HRTOFMS m/z [M+H]$^+$341.2115 (calculated value $C_{22}H_{28}O_3$, 341.2111).

S11, (R,E)-3-(4,8-dimethylnona-3,7-dien-1-yl)-5-(4-nitrophenyl)furan-2(5H)-one, yellow oil, $[\alpha]_D^{25}$+92.0 (c 0.1, MeOH); $^1$H NMR (CDCl$_3$, 500 MHz): δH: 8.07 (d, 7.6, 2H), 7.48 (d, 7.6, 2H), 7.29 (s, 1H), 5.82 (s, 1H), 5.01 (t, 7.5, 1H), 4.97 (t, 7.5, 1H), 2.32 (m, 2H), 2.19 (m, 2H), 1.92 (m, 2H), 1.82 (m, 2H), 1.67 (s, 3H), 1.57 (s, 3H), 1.45 (s, 3H); $^{13}$C NMR (CDCl$_3$, 125 MHz): δC: 174.0, 147.9, 145.9, 141.8, 137.7, 137.2, 131.2, 127.2 (×2), 123.8, 123.6 (×2), 121.4, 89.5, 39.6, 26.6, 25.7, 25.7, 25.5, 17.7, 16.1; positive HRTOFMS m/z [M+H]$^+$356.1852 (calculated value $C_{21}H_{25}NO_4$, 356.1856).

S12, (R,E)-5-(2,5-dimethoxyphenyl)-3-(4,8-dimethylnona-3,7-dien-1-yl)furan-2(5H)-one, yellow oil, $[\alpha]_D^{25}$+46.0 (c 0.1, MeOH); $^1$H NMR (CDCl$_3$, 500 MHz): δH; 7.19 (s, 1H), 6.82 (m, 2H), 6.76 (s, 1H), 6.19 (s, 1H), 5.10 (t, 7.6, 1H), 5.06 (t, 7.6, 1H), 3.86 (s, 3H), 3.72 (s, 3H), 2.35 (m, 2H), 2.26 (m, 2H), 2.03 (m, 2H), 1.97 (m, 2H), 1.67 (s, 3H), 1.59 (s, 3H), 1.58 (s, 3H); $^{13}$C NMR (CDCl$_3$, 125 MHz): δC 176.7, 151.1, 148.8, 137.7, 132.9, 132.1, 123.9, 123.4, 125.3, 123.4, 117.1, 117.1, 113.1, 79.8, 55.8, 56.1, 40.7, 27.6, 26.8, 26.1, 25.8, 17.7, 16.2; positive HRTOFMS m/z [M+H]$^+$371.2218 (calculated value $C_{23}H_{30}O_4$, 371.2217).

S13, (R,E)-5-(2,5-dihydroxyphenyl)-3-(4,8-dimethylnona-3,7-dien-1-yl)furan-2(5H)-one, yellow oil, $[\alpha]_D^{25}$+92.0 (c 0.1, MeOH); $^1$H NMR (CDCl$_3$, 500 MHz): δH: 7.18 (s, 1H), 6.83 (m, 2H), 6.76 (s, 1H), 6.19 (s, 1H), 5.10 (t, 7.6, 1H), 5.06 (t, 7.6, 1H), 2.35 (m, 2H), 2.26 (m, 2H), 2.03 (m, 2H), 1.97 (m, 2H), 1.67 (s, 3H), 1.59 (s, 3H), 1.58 (s, 3H); $^{13}$C NMR (CDCl$_3$, 125 MHz): δC 176.7, 151.3, 148.5, 137.6, 132.8, 132.1, 123.9, 123.4, 125.3, 123.4, 117.1, 117.1, 113.1, 79.8, 40.7, 27.6, 26.8, 26.1, 25.8, 17.7, 16.2; positive HRTOFMS m/z [M+H]$^+$343.1834 (calculated value $C_{21}H_{26}O_4$, 343.1831).

S14, (R,E)-5-(2,6-difluorophenyl)-3-(4,8-dimethylnona-3,7-dien-1-yl)furan-2(5H)-one, yellow oil, $[\alpha]_D^{25}$+89.0 (c 0.1, MeOH); $^1$H NMR (CDCl$_3$, 500 MHz): δH: 7.33 (m, 1H), 7.07 (s, 1H), 6.90 (m, 2H), 6.22 (s, 1H), 5.513 (t, 7.6, 1H), 5.07 (t, 7.6, 1H), 2.41 (m, 2H), 2.32 (m, 2H), 2.04 (m, 2H), 1.99 (m, 2H), 1.66 (s, 3H), 1.61 (s, 3H), 1.59 (s, 3H); $^{13}$C NMR (CDCl$_3$, 125 MHz): δC: 174.0, 158.7, 155.2, 148.6, 135.7, 135.1, 132.6, 132.0, 124.5, 123.5, 117.3, 116.0, 115.8, 79.8, 39.7, 26.6, 25.7, 25.7, 25.4, 17.7, 16.2; positive HRTOFMS m/z [M+H]$^+$347.1817 (calculated value $C_{21}H_{24}F_2O_4$, 347.1817).

S15, (R,E)-3-(4,8-dimethylnona-3,7-dien-1-yl)-5-(3,4,5-trifluorophenyl)furan-2(5H)-one, yellow oil, $[\alpha]_D^{25}$+21.0 (c 0.1, MeOH); $^1$H NMR (CDCl$_3$, 500 MHz): δH; 7.27 (m, 1H), 7.02 (s, 1H), 6.91 (m, 1H), 5.77 (s, 1H), 5.08 (m, 2H), 2.41 (m, 2H), 2.30 (m, 2H), 2.02 (m, 2H), 1.99 (m, 2H), 1.65 (s, 3H), 1.59 (s, 6H); $^{13}$C NMR (CDCl$_3$, 125 MHz): δC: 172.9, 146.4 (×2), 137.2, 134.6, 131.8, 131.6, 124.0 (×2), 122.3 (×2), 110.9, 110.7, 80.2, 39.6, 26.6, 25.7, 25.6, 25.4, 17.7, 16.2; positive HRTOFMS m/z [M+H]$^+$365.1725 (calculated value $C_{21}H_{23}F_3O_4$, 365.1723).

S16, (S,E)-3-(4,8-dimethylnona-3,7-dien-1-yl)-5-phenylfuran-2(5H)-one, yellow oil, $[\alpha]_D^{25}$−49.0 (c 0.1, MeOH); it has the same NMR data with compound S1, positive HRTOFMS m/z [M+H]$^+$311.2008 (calculated value $C_{21}H_{26}O_2$, 311.2006).

S17, (S,E)-3-(4,8-dimethylnona-3,7-dien-1-yl)-5-(naphthalen-2-yl)furan-2 (5H)-one, yellow oil, $[\alpha]_D^{25}$−24.4 (c 0.1, MeOH); it has the same NMR data with compound S2, positive HRTOFMS m/z [M+H]$^+$361.2161 (calculated value $C_{25}H_{28}O_2$, 361.2162).

S18, (S,E)-3-(4,8-dimethylnona-3,7-dien-1-yl)-5-(2-(methoxymethoxy)phenyl) furan-2(5H)-one, yellow oil, $[\alpha]_D^{25}$−61.0 (c 0.1, MeOH); it has the same NMR data with compound S3, positive HRTOFMS m/z [M+H]$^+$371.2215 (calculated value $C_{23}H_{30}O_4$, 371.2217).

S19, (S,E)-3-(4,8-dimethylnona-3,7-dien-1-yl)-5-(2-hydroxyphenyl)furan-2(5H)-one, yellow oil, $[\alpha]_D^{25}$−38.0 (c 0.1, MeOH); it has the same NMR data with compound S4, positive HRTOFMS m/z [M+H]$^+$327.1951 (calculated value $C_{21}H_{26}O_3$, 327.1953).

S20, (S,E)-3-(4,8-dimethylnona-3,7-dien-1-yl)-5-(2-nitrophenyl)furan-2(5H)-one, yellow oil, $[\alpha]_D^{25}$−42.0 (c 0.1, MeOH); it has the same NMR data with compound S5, positive HRTOFMS m/z [M+H]$^+$356.1852 (calculated value $C_{21}H_{25}NO_4$, 356.1856).

S21, (S,E)-3-(4,8-dimethylnona-3,7-dien-1-yl)-5-(p-tolyl)furan-2(5H)-one, yellow oil, $[\alpha]_D^{25}$−38.0 (c 0.1, MeOH); it has the same NMR data with compound S6, positive HRTOFMS m/z [M+H]$^+$325.2160 (calculated value $C_{22}H_{28}O_2$, 325.2162).

S22, (S,E)-3-(4,8-dimethylnona-3,7-dien-1-yl)-5-(4-ethylphenyl)furan-2(5H)-one, yellow oil, $[\alpha]_D^{25}$−32.0 (c 0.1, MeOH); it has the same NMR data with compound S7, positive HRTOFMS m/z [M+H]$^+$339.2322 (calculated value $C_{23}H_{30}O_2$, 339.2319).

S23, (S,E)-3-(4,8-dimethylnona-3,7-dien-1-yl)-5-(4-isopropylphenyl)furan-2(5H)-one, yellow oil, $[\alpha]_D^{25}$−45.0 (c 0.1, MeOH); it has the same NMR data with compound S8, positive HRTOFMS m/z [M+H]$^+$353.2475 (calculated value $C_{24}H_{32}O_2$, 353.2475).

S24, (S,E)-5-(4-(tert-butyl)phenyl)-3-(4,8-dimethylnona-3,7-dien-1-yl)furan-2 (5H)-one, yellow oil, $[\alpha]_D^{25}$−46.0 (c 0.1, MeOH); it has the same NMR data with compound S9, positive HRTOFMS m/z [M+H]$^+$367.2632 (calculated value $C_{25}H_{34}O_2$, 367.2632).

S25, (S,E)-3-(4,8-dimethylnona-3,7-dien-1-yl)-5-(4-methoxyphenyl)furan-2(5H)-one, yellow oil, $[\alpha]_D^{25}$−62.0 (c 0.1, MeOH); it has the same NMR data with compound S10, positive HRTOFMS m/z [M+H]$^+$341.2115 (calculated value $C_{22}H_{28}O_3$, 341.2111).

S26, (S,E)-3-(4,8-dimethylnona-3,7-dien-1-yl)-5-(4-nitrophenyl)furan-2(5H)-one, yellow oil, $[\alpha]_D^{25}$−67.0 (c 0.1, MeOH); it has the same NMR data with compound S11, positive HRTOFMS m/z [M+H]$^+$356.1858 (calculated value $C_{21}H_{25}NO_4$, 356.1856).

S27, (S,E)-5-(2,5-dimethoxyphenyl)-3-(4,8-dimethylnona-3,7-dien-1-yl)furan-2(5H)-one, yellow oil, $[\alpha]_D^{25}$−57.0 (c 0.1, MeOH); it has the same NMR data with compound S12, positive HRTOFMS m/z [M+H]$^+$371.2215 (calculated value $C_{23}H_{30}O_4$, 371.2217).

S28, (S,E)-5-(2,5-dihydroxyphenyl)-3-(4,8-dimethylnona-3,7-dien-1-yl)furan-2(5H)-one, yellow oil, $[\alpha]_D^{25}$−88.0 (c 0.1, MeOH); it has the same NMR data with compound S13, positive HRTOFMS m/z [M+H]$^+$343.1830 (calculated value $C_{21}H_{26}O_4$, 343.1831).

S29, (S,E)-5-(2,6-difluorophenyl)-3-(4,8-dimethylnona-3,7-dien-1-yl)furan-2(5H)-one, yellow oil, $[\alpha]_D^{25}$−84.0 (c 0.1, MeOH); it has the same NMR data with compound S14, positive HRTOFMS m/z [M+H]$^+$347.1817 (calculated value $C_{21}H_{24}F_2O_4$, 347.1817).

S20, (S,E)-3-(4,8-dimethylnona-3,7-dien-1-yl)-5-(3,4,5-trifluorophenyl)furan-2(5H)-one, yellow oil, $[\alpha]_D^{25}$−32.0 (c 0.1, MeOH); it has the same NMR data with compound S15, positive HRTOFMS m/z [M+H]$^+$365.1723 (calculated value $C_{21}H_{23}F_3O_4$, 365.1723).

S31, (E)-5-(2,5-dihydroxyphenyl)-3-(4,8-dimethylnona-3,7-dien-1-yl)-5-meth oxyfuran-2(5H)-one, yellow oil, $[\alpha]_D^{25}$−2.0 (c 0.1, MeOH); $^1$H NMR (MeOD, 500 MHz): δH; 7.38 (s, 1H), 6.93 (d, 2.8, 1H), 6.75 (d, 8.6, 1H), 6.71 (dd, 8.6, 2.8), 5.11 (t, 7.1, 1H), 5.06 (t, 6.8, 1H), 3.52 (s, 3H), 2.32 (m, 2H), 2.27 (m, 2H), 2.00 (m, 2H), 1.92 (m, 2H), 1.68 (s, 3H), 1.61 (s, 6H); $^{13}$C NMR (MeOD, 125 MHz): δC: 171.6, 151.1, 148.7, 146.9, 137.1, 135.8, 131.6, 125.0, 123.8, 123.6, 118.3, 118.0, 114.1, 107.6, 56.9, 43.0, 27.2, 26.1, 25.8, 25.7, 17.7, 16.1; positive HRTOFMS m/z [M+H]$^+$373.2011 (calculated value $C_{22}H_{28}O_5$ 373.2010)

S32, (2Z,5E)-2-(2-(2,5-dihydroxyphenyl)-2-oxoethylidene)-6,10-dimethylundeca-5,9-dienoic acid, yellow oil, $[\alpha]_D^{25}$+3.0 (c 0.1, MeOH); $^1$H NMR (MeOD, 500 MHz): δH; 7.70 (s, 1H), 7.13 (d, 2.7, 1H), 7.04 (dd, 8.8, 2.7), 6.82 (d, 8.8, 1H), 5.06 (t, 7.1, 1H), 4.99 (t, 6.9, 1H), 2.65 (m, 2H), 2.20 (m, 2H), 1.94 (m, 2H), 1.75 (m, 2H), 1.62 (s, 3H), 1.58 (s, 3H), 1.54 (s, 3H); $^{13}$C NMR (CDCl$_3$, 125 MHz): δC: 198.7, 170.1, 157.2, 150.7, 145.9, 137.6, 132.9, 126.6, 125.4, 124.0, 121.3, 119.9, 115.9, 40.6, 29.2, 28.5, 27.6, 25.9, 16.2, 15.8; positive HRTOFMS m/z [M+H]$^+$359.1853 (calculated value $C_{21}H_{26}O_5$, 359.1853).

S33, (2Z,5E,9E)-2-(2-(2,5-dihydroxyphenyl)ethylidene)-11-hydroxy-6,10-dimethylundeca-5,9-dienoic acid, yellow oil, $[\alpha]_D^{25}$+2.0 (c 0.1, MeOH); $^1$H NMR (MeOD, 500 MHz): δH; 6.64 (d, 8.5, 1H), 6.61 (d, 2.8, 1H), 6.52 (dd, 8.5, 2.8), 5.98 (t, 7.1, 1H), 5.39 (t, 7.1, 1H), 5.14 (t, 7.3, 1H), 3.94 (s, 2H), 3.69 (d, 7.7, 2H) 2.33 (m, 2H), 2.19 (m, 2H), 2.10 (m, 2H), 2.00 (m, 2H), 1.66 (s, 3H), 1.61 (s, 3H); $^{13}$C NMR (MeOD, 125 MHz): δC: 172.3, 151.2, 149.3, 140.5, 136.7, 135.8, 133.3, 128.0, 126.8, 124.6, 117.8, 116.9, 114.8, 69.0, 40.6, 35.9, 31.5, 28.5, 27.3, 16.2, 13.7; positive HRTOFMS m/z [M+H]$^+$361.2010 (calculated value $C_{21}H_{28}O_5$, 361.2010).

S34, (2Z,5E)-2-(2-(2,5-dihydroxyphenyl)ethylidene)-6,10-dimethylundeca-5,9-dienoic acid, yellow oil, $[\alpha]_D^{25}$+1.0 (c 0.1, MeOH); $^1$H NMR (MeOD, 500 MHz): δH; 6.64 (d, 8.5, 1H), 6.61 (d, 2.8, 1H), 6.52 (dd, 8.5, 2.8), 5.98 (t, 7.1, 1H), 5.13 (t, 7.3, 1H), 5.10 (t, 7.3, 1H), 3.69 (d, 7.7, 2H), 2.33 (m, 2H), 2.19 (m, 2H), 2.05 (m, 2H), 2.00 (m, 2H), 1.68 (s, 3H), 1.62 (s, 3H), 1.61 (s, 3H); $^{13}$C NMR (MeOD, 125 MHz): δC: 172.3, 151.2, 149.3, 140.5, 136.7, 133.3, 128.0, 125.5, 124.4, 117.8, 116.9, 114.8, 40.4 35.9, 31.5, 28.5, 27.7, 25.9, 17.8, 16.2; positive HRTOFMS m/z [M+H]$^+$345.2063 (calculated value $C_{21}H_{28}O_4$, 345.2060).

S35, (2Z,5E,9E)-2-(2-(2,5-dihydroxyphenyl)ethylidene)-6,10-dimethyl-11-oxo undeca-5,9-dienoic acid, yellow oil, $[\alpha]_D^{25}$ −4.0 (c 0.1, MeOH); $^1$H NMR (MeOD, 500 MHz): δH; 6.64 (d, 8.5, 1H), 6.61 (d, 2.8, 1H), 6.52 (dd, 8.5, 2.8), 5.98 (t, 7.1, 1H), 5.39 (t, 7.1, 1H), 5.14 (t, 7.3, 1H), 3.69 (d, 7.7, 2H) 2.33 (m, 2H), 2.19 (m, 2H), 2.10 (m, 2H), 2.00 (m, 2H), 1.66 (s, 3H), 1.61 (s, 3H); $^{13}$C NMR (MeOD, 125 MHz): δC: 194.0, 172.3, 151.2, 149.3, 140.5, 136.7, 135.8, 133.3, 128.0, 126.8, 124.6, 117.8, 116.9, 114.8, 40.6, 35.9, 31.5, 28.5, 27.3, 16.2, 13.7; positive HRTOFMS m/z [M+H]$^+$359.1854 (calculated value $C_{21}H_{26}O_5$, 359.1854).

S36, (E)-2-(2-(2,5-dihydroxyphenyl)-2-oxoethyl)-6,10-dimethylundeca-5,9-dienoic acid, yellow oil, $[\alpha]_D^{25}$ −3.0 (c 0.1, MeOH); $^1$H NMR (MeOD, 500 MHz): δH; 7.38 (d, 2.9, 1H), 7.08 (dd, 8.9, 2.9, 1H), 6.79 (d, 8.9, 1H), 5.18 (t, 7.1, 1H), 5.10 (t, 7.1, 1H), 3.50 (dd, 17.9, 9.2, 1H), 3.16 (dd, 17.9, 4.4, 1H), 3.03 (m, 2H), 2.14 (m, 2H), 2.05 (m, 2H), 1.99 (m, 2H), 1.87 (m, 2H), 1.64 (s, 3H), 1.61 (s, 3H), 1.58 (s, 3H); $^{13}$C NMR (MeOD, 125 MHz): δC: 205.0, 176.4, 156.3, 150.2, 136.2, 131.6, 125.6, 125.0, 124.3, 120.0, 119.3, 115.4, 40.3, 40.1, 32.6, 27.3, 26.1, 25.7, 17.7, 16.1; positive HRTOFMS m/z [M+H]$^+$361.2013 (calculated value $C_{21}H_{28}O_5$, 361.2010).

S37, (R)-5-(2,5-dihydroxyphenyl)-3-(4-methylpent-3-en-1-yl)furan-2(5H)-one, yellow oil, $[\alpha]_D^{25}$ +42.1 (c 0.1, MeOH); $^1$H NMR (MeOD, 500 MHz): δH; 7.35 (d, 1.4, 1H), 6.76 (d, 8.6, 1H), 6.65 (dd, 8.6, 2.9, 1H), 6.53 (d, 2.9, 1H), 6.20 (d, 1.4, 1H), 5.12 (t, 7.1, 2H), 2.30 (m, 2H), 2.28 (m, 2H), 1.64 (s, 3H), 1.57 (s, 3H); $^{13}$C NMR (MeOD, 125 MHz): δC: 174.6, 151.3, 149.5, 148.2, 133.1, 132.7, 123.9, 123.6, 117.0, 116.8, 113.2, 78.3, 26.6, 25.9, 25.7, 17.7; positive HRTOFMS m/z [M+H]$^+$275.1281 (calculated value $C_{16}H_{18}O_4$, 275.1281).

S38, (S)-5-(2,5-dihydroxyphenyl)-3-(4-methylpent-3-en-1-yl)furan-2(5H)-one, colorless oil, $[\alpha]_D^{25}$ −35.1 (c 0.1, MeOH); it has the same NMR data with compound S37, positive HRTOFMS m/z [M+H]+275.1284 (calculated value $C_{16}H_{18}O_4$, 275.1281).

Example 4, A-Glucosidase Inhibitory Activity Test of Compounds S1-S38 In Vitro

Test solutions: accurately weigh the 38 compounds S1-S38 prepared in example 3, then add DMSO to make solution of 5 mM used for activity test (final concentration range is 0.05-50 μM, after the compound is dissolved in a little DMSO, dilute it with distilled water to a corresponding concentration, and the final volume fraction of DMSO is <0.1%); atorvastatin is used as positive control (final concentration are 4000 μM, 1000 μM, 250 μM and 62.5 μM respectively, after the compound is dissolved in a little DMSO, dilute it with distilled water to a corresponding concentration, and the final volume fraction of DMSO is <0.1%).

Add 25 μL α-glucosidase water solution (0.2 U/mL) and 175 μL phosphate buffer (50 mM, pH 7.0) into 25 μL different concentration of the above test solutions. The mixed solution is standed for 10 min at room temperature, and then 25 μL 4-nitrophenyl-α-D-glucopyranoside water solution (2.5 mM) is added into the mixed solution. After the solution is incubated at 37□ for 30 min and centrifuged at 5000 rpm for 5 minutes, 150 uL supernatant is added into 96-well plates and the absorbance is detected at 405 nm.

Blank group: the test solution is replaced by 25 μL phosphate buffer (50 mM, pH 7.0); blank control group: the test solution is replaced by 25 μL phosphate buffer (50 mM, pH 7.0), meanwhile α-glucosidase water solution is replaced by 25 μL phosphate buffer (50 mM, pH 7.0); sample control group: α-glucosidase water solution is replaced by 25 μL phosphate buffer (50 mM, pH 7.0).

Repeat each of the above experiment groups for 3 times, and then average the results. The following formula is used to calculate the α-glucosidase inhibition rate of the samples:

inhibition rate (%)=[1−(absorbance of test solution−absorbance of sample control group)/(absorbance of blank group−absorbance of blank control group)×100%

Analyzes the experimental data statistically, and IC$_{50}$ values of the samples are shown in table 2.

$$IC_{50}=[C_L(I_H-50)+C_H(50-I_L)]/(I_H-I_L)$$

$C_L$: low concentration value; $C_H$: high concentration value; $I_H$: inhibition rate in high concentration; $I_L$: inhibition rate in low concentration It has shown that all of the compounds have strong α-glucosidase inhibitory activity, and the activities of the compounds are stronger than that of positive control drug atorvastatin.

TABLE 2

Testing results of α-glucosidase inhibitory activities of compounds S1-S38

| | α-glucosidase inhibitory activity |
|---|---|
| S1 | 0.18 |
| S2 | 7.40 |
| S3 | 8.65 |
| S4 | 0.21 |
| S5 | 0.09 |
| S6 | 1.06 |
| S7 | 0.58 |
| S8 | 56.2 |
| S9 | 0.16 |
| S10 | >50 |
| S11 | 34.20 |
| S12 | 11.52 |
| S13 | 0.27 |
| S14 | 3.72 |
| S15 | 1.27 |
| S16 | 0.23 |
| S17 | 6.32 |
| S18 | 8.20 |
| S19 | 0.52 |
| S20 | 0.21 |
| S21 | 1.03 |
| S22 | 0.92 |
| S23 | 49.2 |
| S24 | 0.23 |
| S25 | 52.10 |
| S26 | 30.26 |
| S27 | 15.28 |
| S28 | 0.42 |
| S29 | 3.95 |
| S30 | 1.25 |
| S31 | 3.23 |
| S32 | 5.43 |
| S33 | 12.23 |
| S34 | 0.98 |
| S35 | 12.3 |
| S36 | 3.2 |
| S37 | 1.32 |
| S38 | 1.23 |
| atorvastatin | 273.1 |

Example 5, HMG-CoA Reductase Inhibitory Activity Test of Compounds S1-S38 In Vitro Test solutions: accurately weigh the 38 compounds S1-S38 prepared in example 3, and then add DMSO to make the solution of 10 mM used for activity test (final concentration range is 1-100 μM, after the compound is dissolved in a little DMSO, dilute it with distilled water to a corresponding concentration, and the final volume fraction of DMSO is <0.1%); atorvastatin is used as positive control (final concentration are 100 μM, 50 μM, 25 μM and 12.5 μM respectively, after the compound is dissolved in a little DMSO, dilute it with distilled water to a corresponding concentration, and the final volume fraction of DMSO is <0.1%).

Add 25 μL HMG-CoA reductase water solution (0.2 U/mL), 25 μL NADPH water solution (0.2 U/mL) and 24 μL phosphate buffer (50 mM, pH 7.0) into 1 μL different concentration of the above test solution. The mixed solution is standed for 10 min at room temperature, and then 25 μL HMG-CoA is added into the mixed solution. After the solution is incubated at 37∞ for 30 min and centrifuged at 5000 rpm for 5 minutes, 80 uL supernatant is added into 96-well plates and the absorbance is detected at 550 nm.

Repeat each of the above experiment groups for 3 times, and then average the results. The following formula is used to calculate the HMG-CoA reductase inhibition rate of the samples:

inhibition rate (%)=[1−(absorbance of test solution−absorbance of sample control group)/(absorbance of blank group−absorbance of blank control group)×100%

Analyzes the experimental data statistically, and $IC_{50}$ values of the samples are shown in table 3. It has shown that all of the compounds have strong HMG-CoA reductase inhibitory activity, and the activities of the compounds are stronger than that of positive control drug atorvastatin.

TABLE 3

Testing results of HMG-CoA reductase inhibitory activities of compounds S1-S38

|  | HMG-CoA reductase inhibitory activity |
| --- | --- |
| S1 | 3.8 |
| S2 | 49.8 |
| S3 | 8.9 |
| S4 | 4.7 |
| S5 | 18.9 |
| S6 | 8.1 |
| S7 | 4.2 |
| S8 | >100 |
| S9 | 16.4 |
| S10 | 1.2 |
| S11 | 7.4 |
| S12 | 4.4 |
| S13 | 7.9 |
| S14 | 25.1 |
| S15 | 38.2 |
| S16 | 3.6 |
| S17 | 42.2 |
| S18 | 6.2 |
| S19 | 5.5 |
| S20 | 13.8 |
| S21 | 12.5 |
| S22 | 4.2 |
| S23 | 87.2 |
| S24 | 15.2 |
| S25 | 1.5 |
| S26 | 7.5 |
| S27 | 4.4 |
| S28 | 8.9 |
| S29 | 16.8 |
| S30 | 24.2 |
| S31 | 32.3 |
| S32 | 5.4 |
| S33 | 32.9 |
| S34 | 12.6 |
| S35 | 20.7 |
| S36 | 4.2 |
| S37 | 65.2 |
| S38 | 12.5 |
| atorvastatin | 31.2 |

Example 6, Protein Tyrosine Phosphatase 1B (PTP-1B) Inhibitory Activity Test of Compounds S1-S38 In Vitro Test solutions: accurately weigh the 38 compounds S1-S38 prepared in example 3, and then add DMSO to make the solution of 200 μM used for activity test (final concentration range is 1-50 μM, after the compound is dissolved in a little DMSO, dilute it with distilled water to a corresponding concentration, and the final volume fraction of DMSO is <0.1%); sodium vanadate is used as positive control (final concentration are 20 μM, 10 μM, 5 μM, 2 μM and 1 μM respectively, after the compound is dissolved in a little DMSO, dilute it with distilled water to a corresponding concentration, and the final volume fraction of DMSO is <0.1%).

Experimental procedure: the following reagents are added into 96-well plates in sequence and the mixture ratios of different groups are as followings:

Test group: 50 μL compound solution+50 μL 170 μg/mL PTP-1B solution

Positive control group: 50 μL sodium vanadate solution+50 μL 170 μg/mL PTP-1B solution Blank group: 50 μL buffer solution+50 μL 170 μg/mL PTP-1B solution Background group: 50 μL compound solution+50 μL buffer solution After adding the reagents, the 96-well plate is standed for 10 min at room temperature to make the compound and the enzyme react completely. Add 50 μL 1 mM pNPP solution which is used as substrate and incubate the mixed solution at 37□ for 30 min. Then add 50 μL 3M NaOH into each well of the plate to stop the reaction and the optical density is detected at 550 nm.

Analyzes the experimental data statistically, and $IC_{50}$ values of the samples are shown in table 4. It has shown that all of the compounds have certain PTP-1B inhibitory activity.

TABLE 4

Testing results of PTP-1B inhibitory activities of compounds S1-S38

|  | PTP-1B inhibitory activity, $IC_{50}$, μM |
| --- | --- |
| S1 | 10.5 |
| S2 | 13.1 |
| S3 | 7.8 |
| S4 | 11.1 |
| S5 | 5.3 |
| S6 | 5.6 |
| S7 | 15.5 |

TABLE 4-continued

Testing results of PTP-1B inhibitory activities of compounds S1-S38

| | PTP-1B inhibitory activity, IC$_{50}$, μM |
|---|---|
| S8 | 12.7 |
| S9 | 15.8 |
| S10 | 10.1 |
| S11 | 8.1 |
| S12 | 11.8 |
| S13 | 8.9 |
| S14 | 3.7 |
| S15 | 25.4 |
| S16 | 12.5 |
| S17 | 10.1 |
| S18 | 8.2 |
| S19 | 11.5 |
| S20 | 4.7 |
| S21 | 5.8 |
| S22 | 16.4 |
| S23 | 9.6 |
| S24 | 17.6 |
| S25 | 16.5 |
| S26 | 9.8 |
| S27 | 12.3 |
| S28 | 9.5 |
| S29 | 4.4 |
| S30 | 21.1 |
| S31 | 15.4 |
| S32 | 7.6 |
| S33 | 4.5 |
| S34 | 12.9 |
| S35 | 12.3 |
| S36 | 11.4 |
| S37 | 12.3 |
| S38 | 9.8 |
| sodium vanadate | 1.4 |

Example 7, Aldose Reductase Inhibitory Activity Test of Compounds S1-S38 In Vitro Test solutions: accurately weigh the 38 compounds S1-S38 prepared in example 3, and then add DMSO to make the solution of 1 mM used for activity test (final concentration range is 1-100 μM, after the compound is dissolved in a little DMSO, dilute it with distilled water to a corresponding concentration, and the final volume fraction of DMSO is <0.1%), epalrestat is used as positive control (final concentration are 20 μM, 10 μM, 5 μM, 2 μM and 1 μM respectively, after the compound is dissolved in a little DMSO, dilute it with distilled water to a corresponding concentration, and the final volume fraction of DMSO is <0.1%).

Experimental procedure: the following reagents are added into 96-well plates in sequence and the mixture ratios of different groups are as followings:

Test group: 10 μL compound solution+25 μL (0.1 mM) NADPH solution+25 μL PBS buffer solution+15 μL aldose reductase diluent Positive control group: 10 μL epalrestat solution+25 μL (0.1 mM) NADPH solution+25 μL PBS buffer solution+15 μL aldose reductase diluent Blank group: 25 μL (0.1 mM) NADPH solution+35 μL PBS buffer solution+15 μL aldose reductase diluent Background group: 25 μL (0.1 mM) NADPH solution+60 μL PBS buffer solution+15 μL aldose reductase diluent After adding the reagents, the 96-well plate is standed for 10 min at room temperature to make the compound and the enzyme react completely. Add 25 μL 10 mM D, L glyceraldehyde solution which is used as substrate into the groups except for background group, and incubate the solution at 37□ for 30 min. Then detect the optical density of each well at 340 nm.

Analyzes the experimental data statistically, and IC$_{50}$ values of the samples are shown in table 5. It has shown that all of the compounds have certain aldose reductase inhibitory activity.

TABLE 5

Testing results of aldose reductase inhibitory activities of compounds S1-S38

| | aldose reductase inhibitory activity, IC$_{50}$, μM |
|---|---|
| S1 | 56.1 |
| S2 | 19.8 |
| S3 | 38.3 |
| S4 | 23.5 |
| S5 | 8.5 |
| S6 | 63.2 |
| S7 | 59.0 |
| S8 | 84.4 |
| S9 | 1.4 |
| S10 | >100 |
| S11 | 4.9 |
| S12 | 26.1 |
| S13 | 1.8 |
| S14 | 32.1 |
| S15 | 54.9 |
| S16 | 58.2 |
| S17 | 20.2 |
| S18 | 40.2 |
| S19 | 25.4 |
| S20 | 9.5 |
| S21 | 55.1 |
| S22 | 55.6 |
| S23 | 93.1 |
| S24 | 1.2 |
| S25 | 101.2 |
| S26 | 5.3 |
| S27 | 25.2 |
| S28 | 1.6 |
| S29 | 33.5 |
| S30 | 53.4 |
| S31 | 87.6 |
| S32 | 34.9 |
| S33 | 23.1 |
| S34 | 8.7 |
| S35 | 5.6 |
| S36 | 6.3 |
| S37 | 12.6 |
| S38 | 67.5 |
| epalrestat | 2.3 |

Example 8, Dipeptidyl Peptidase-4 Inhibitory Activity Test of Compounds S1-S38 In Vitro Test solutions: accurately weigh the 38 compounds S1-S38 prepared in example 3, and then add DMSO to make the solution of 1 mM used for activity test (final concentration range is 1-100 μM, after the compound is dissolved in a little DMSO, dilute it with distilled water to a corresponding concentration, and the final volume fraction of DMSO is <0.1%); sitagliptin phosphate is used as positive control (final concentration are 20 μM, 10 μM, 5 μM, 2 μM and 1 μM respectively, after the compound is dissolved in a little DMSO, dilute it with distilled water to a corresponding concentration, and the final volume fraction of DMSO is <0.1%).

The above compounds are detected by DPP-4 inhibitor screening kit.

Analyzes the experimental data statistically, and $IC_{50}$ values of the samples are shown in table 6. It has shown that all of the compounds have certain dipeptidyl peptidase-4 inhibitory activity.

TABLE 6

Testing results of dipeptidyl peptidase-4 inhibitory activities of compounds S1-S38

| | dipeptidyl peptidase-4 inhibitory activity, $IC_{50}$, μM |
|---|---|
| S1 | 12.2 |
| S2 | 12.5 |
| S3 | 14.5 |
| S4 | 21.2 |
| S5 | 20.9 |
| S6 | 31.5 |
| S7 | 9.2 |
| S8 | 9.4 |
| S9 | 19.1 |
| S10 | 18.2 |
| S11 | 10.2 |
| S12 | 8.8 |
| S13 | 4.5 |
| S14 | 24.5 |
| S15 | 12.1 |
| S16 | 12.0 |
| S17 | 13.6 |
| 818 | 14.4 |
| S19 | 20.2 |
| S20 | 20.8 |
| S21 | 16.5 |
| S22 | 9.5 |
| S23 | 8.8 |
| S24 | 15.8 |
| S25 | 18.5 |
| S26 | 10.6 |
| S27 | 8.6 |
| S28 | 6.8 |
| S29 | 23.5 |
| S30 | 11.6 |
| S31 | 15.4 |
| S32 | 21.2 |
| S33 | 18.7 |
| S34 | 15.2 |
| S35 | 7.8 |
| S36 | 21.8 |
| S37 | 15.4 |
| S38 | 12.9 |
| sitagliptin phosphate | 1.5 |

Example 9, Effect of Compounds S13 and S28 on Blood Lipid of Rats Fed with High Fat Diet Materials: accurately weigh the 2 compounds S13 and S28 prepared in example 1, and then add 0.5% CMC-Na to make the solution of 10 mg/ml used for activity test. Rats are purchased from Beijing Vital River Laboratory Animal Technology Co., Ltd. Experiments are carried out after adapting to the environment (T=20-24□, constant humidity: 50-60%, 12 hours light exposure (8:00-20:00), soundproof, free feeding and drinking) for 1 week. Serum total cholesterol kit (batch number 20131112), low density lipoprotein LDL-C kit (batch number 20140114), high density lipoprotein HDL-C kit (batch number 20140413), triglyceride TG kit (batch number 20131226), superoxide dismutase SOD kit (batch number 20140213) and glutamic-pyruvic transaminase ALT kit (batch number 20131006) are purchased from Nanjing Jiancheng Bioengineering Institute.

Methods: after being acclimatized for 1 week, the 200±20 g healthy male SD rats are randomly divided into 4 groups of 8 animals in each. The control group is fed with normal diet, while the other groups are fed with high-fat diet, which is normal diet with 1% cholesterol, 0.2% pig bile sal, 10% lard and 10% egg yolk powder. After being fed for 3 weeks, 10 mg/ml extract solution of 1 ml (which corresponds to 50 mg/kg) is given to different groups of rats by intragastric administration for 10 days successively, and the control group and model group are given with equal amounts of saline. After the last administration, blood is taken to be centrifuged at 3000 rpm in 4□, and then detect serum total cholesterol, low density lipoprotein and triglyceride TG Results: comparing with the control group and model group, the 2 compounds can significantly improve the blood lipid status of rats, and have a good reverse effect to glutamic-pyruvic transaminase (ALT) of rat serum. It suggests that the compounds are effective against liver damage caused by hyperlipemia, which is probably achieved by enhancing the activity of SOD, and the results are shown in table 7.

TABLE 7

Effect of compounds S13 and S28 on blood lipid of rats fed with high fat diet

| group | TC mmol/L | LDL-C mmol/L | HDL-C mmol/L | TG mmol/L | SOD U/L | ALT U/L |
|---|---|---|---|---|---|---|
| control group | 1.38 | 0.21 | 1.12 | 0.18 | 2.52 | 41.3 |
| model group | 3.56## | 0.52## | 0.92 | 0.62## | 1.90 # | 93.4## |
| S13 | 2.13* | 0.36** | 0.99 | 0.44* | 2.04 | 61.3* |
| S28 | 1.98** | 0.38** | 0.97 | 0.45* | 2.10* | 72.1* |

Comparing with normal group, #P < 0.05, ##P < 0.01;
Comparing with model group, *P < 0.05, **P < 0.01.

Example 10, Activity Study of Compounds S13 and S28 on Blood Sugar of Normal Mice Materials: accurately weigh the 2 compounds S13 and S28 prepared in example 1, and then add 0.5% CMC-Na to make the solution of 10 mg/ml used for activity test. Kunming species mice of SPF level are purchased from Beijing Vital River Laboratory Animal Technology Co., Ltd. Experiments are carried out after adapting to the environment (T=20-24□, constant humidity: 50-60%, 12 hours light exposure (8:00-20:00), soundproof, free feeding and drinking) for 1 week. Blood glucose determination kit (batch number 20140403) is purchased from Nanjing Jiancheng Bioengineering Institute.

Methods: after being acclimatized for 1 week, the 20±2 g Kunming species mice are randomly divided into 3 groups of 12 animals in each. 10 mg/ml extract solution of 0.1 ml (which corresponds to 50 mg/kg) is given to different groups of mice by intragastric administration for 10 days successively, and the control group is given with equal amounts of saline. After the last administration, the mice are fasted for 10 hours and blood is collected from orbit, then detect the blood sugar by blood glucose determination kit.

Results: comparing with the control group and model group, the blood sugar levels of the groups of the 2 compounds have no statistical differences, and it suggests that the 2 compounds have no effects on blood sugar of normal mice, which is shown in table 8.

TABLE 8

Effects of compounds S13 and S28 on blood sugar of normal mice

| group | blood sugar mmol/L |
|---|---|
| control group | 4.98 |
| S13 | 4.21 |
| S28 | 4.02 |

Example 11, Activity Study of Compounds S13 and S28 on Blood Sugar of Hyperglycemia Mice Induced by Alloxan Materials: accurately weigh the 2 compounds S13 and S28 prepared in example 1, and then add 0.5% CMC-Na to make the solution of 10 mg/ml used for activity test. SPF mice are purchased from Beijing Vital River Laboratory Animal Technology Co., Ltd. Experiments are carried out after adapting to the environment (T=20-24□, constant humidity: 50-60%, 12 hours light exposure (8:00-20:00), soundproof, free feeding and drinking) for 1 week. Blood glucose determination kit (batch number 20140403) is purchased from Nanjing Jiancheng Bioengineering Institute.

Methods: after being acclimatized for 1 week, 10 randomly selected Kunming species male mice of SPF level of 20±2 g are used as control group, while the other 50 mice are given alloxan to make model by intraperitoneal injection according to body weight 220 mg/kg. After 72 h, blood is collected from mice orbit and the mice whose blood sugar range is 8.8-20 mmol/L are selected for further experiments. In this experiment, there are 32 mice being selected and they are divided into model group and treated group randomly according to blood sugar level. 10 mg/ml extract solution of 0.1 ml (which corresponds to 50 mg/kg) is given to treated group by intragastric administration for 10 days successively, and the control group and model group are given with equal amounts of saline. After the last administration, the mice are fasted for 10 hours and blood is collected from orbit, then detect the blood sugar by blood glucose determination kit.

Results: which has been shown in table 9 that before administration the blood sugar of all the mice rise obviously except for normal control group, that is, alloxan model has been successfully established. After administration, the blood sugar slightly decrease, which suggests that compounds S13 and S28 can significantly decrease the blood sugar level of hyperglycemic mice, thus they can be used in treatment of diabetes and diabetic complication.

TABLE 9

Effects of compounds S13 and S28 on blood sugar of hyperglycemia mice induced by alloxan

| group | blood sugar (mmol/L) before administration | blood sugar (mmol/L) after administration | group | blood sugar (mmol/L) before administration | blood sugar (mmol/L) after administration |
|---|---|---|---|---|---|
| Control group | 4.96 | 4.88 | S13 | 14.50 | 5.11** |
| Model group | 15.34## | 15.19## | S16 | 15.25 | 6.12** |

Comparing with normal group, #P < 0.05, ##P < 0.01;
comparing with model group, *P < 0.05, **P < 0.01

Example 12, Effects of Compounds S13 and S28 on Blood Sugar of Hyperglycemia KK-A$^y$ Mice Materials: accurately weigh the 2 compounds S13 and S28 discussed in example 2, and then add 0.5% CMC-Na to make the solution of 5 mg/ml used for activity test. KK-A$^y$ mice are purchased from Chinese Academy of Medical Sciences & Peking Union Medical College Institute of Animal Studies. Experiments are carried out after adapting to the environment (T=20-24° C., constant humidity: 50-60%, 12 hours light exposure (8:00-20:00), soundproof, free feeding and drinking) for 1 week. Glucometer is purchased from Roche.

Methods: 10 male C57 mice of 6-8 weeks of 20-22 g are used as normal control group (1). Detect the fasting glucose of male KK-A$^y$ mice, which are 6-8 weeks with the weight of 28-32 g, and divide them into different groups according to the blood sugar level and body weight: (2) model control group, (3) which is administered by compound S13 with the dose of 1 mg/kg, (4) which is administered by compound S13 with the dose of 5 mg/kg, (5) which is administered by compound S13 with the dose of 10 mg/kg, (6) which is administered by compound S13 with the dose of 20 mg/kg, (7) which is administered by compound S28 with the dose of 1 mg/kg, (8) which is administered by compound S28 with the dose of 5 mg/kg, (9) which is administered by compound S28 with the dose of 10 mg/kg, (10) which is administered by compound S28 with the dose of 20 mg/kg, (11) which is administered by metformin with the dose of 8 g/kg, (12) which is administered by compound S13 with the dose of 2.5 mg/kg and metformin with the dose of 4 g/kg, (13) which is administered by compound S13 with the dose of 5 mg/kg and metformin with the dose of 4 g/kg, (14) which is administered by compound S28 with the dose of 2.5 mg/kg and metformin with the dose of 4 mg/kg, (15) which is administered by compound S28 with the dose of 5 mg/kg and metformin with the dose of 4 mg/kg. Each group has 8 mice, and is administrated successively for 3 weeks. Model control group is given with equal amounts of 0.5% CMC-Na.

Metformin is the preferred drug in clinical treatment of diabetes, and it can increase the insulin sensitivity by decreasing hepatic glucose output, reducing the glucose absorption of intestinal tract and increasing the uptake and utilization of peripheral blood sugar. However, metformin will induce the injury of liver and kidney. Compound S13 provided by the present application can increase the insulin sensitivity because it has strong inhibitory action on PTP1-B, DPP-4, so it is possible to combine the two drugs, which can not only increase the insulin sensitivity but also reduce the injury of liver and kidney.

Determination Index:

1) Effects of drugs on blood sugar: at the first day after administration, the mice are fasted for 2 hours and blood is collected (0 h) to detect the fasting blood sugar. After the compound is given to the mice by intragastric administration for 30 min, blood is collected from tip of tail to detect the blood sugar level.

2) Effects on body weight and blood sugar: the body weight of mice are recorded at the 2th, 5th, 8th, 11th, 14th, 17th, 20th day after administration, and blood is collected from tip of tail to detect the blood sugar level (see table 10).

3) Glucose tolerance test (OGTT): glucose tolerance is detected at the 12th day after administration. The mice are fasted for 12 hours and blood is collected (0 h). After being given with glucose (2.0 g/kg) by oral administration, blood is collected from tip of tail to detect the blood sugar level after 30 min, 60 min and 120 min respectively (see table 11).

4) After the last administration, the mice are executed under anesthesia, and blood is taken to be centrifuged at 3000 rpm in 4□. Serum total cholesterol, low density lipoprotein and triglyceride TG are detected.

5) After the last administration, the liver is taken to be fixed into formalin and the tissue is sliced for observation.

The results have shown that compounds S13 and S28 have significant effects on blood sugar of hyperglycemia mice, have litter effect on body weight and are effective in reducing the glucose load mice (see table 10 and table 11). The curative effect is more obvious when combining the compounds with metformin. Furthermore, the combination has a report function of live injury caused by metformin, thus the compounds can be used in preparing drugs for treating diabetes type II, or treating diabetes type II by combination with metformin, or playing adjuvant function during/after treatment.

TABLE 11-continued

Effects of compounds S13 and S28 on glucose tolerance of hyperglycemia KK-A$^y$ mice

| group | 0 min | 30 min | 60 min | 120 min |
|---|---|---|---|---|
| 10 | 6.9** | 14.3** | 12.4** | 11.9** |
| 11 | 6.5** | 12.8** | 10.47** | 7.41** |
| 12 | 5.8** | 8.8** | 7.9** | 5.2** |
| 13 | 5.4** | 8.5** | 7.32** | 5.94** |
| 14 | 5.3** | 9.4** | 7.7** | 6.4** |
| 15 | 5.3** | 8.2** | 7.3** | 6.7** |

Comparing with normal group, #P < 0.05, ##P < 0.01;
comparing with model group, *P < 0.05, **P < 0.01.

Comparing with the control group and model group, the compounds can significantly improve the blood lipid status of rats, and have good reverse effect to glutamic-pyruvic transaminase (ALT) of rat serum. It suggests that the compounds are effective against liver damage caused by hyper-

TABLE 10

Effects of compounds S13 and S28 on blood sugar of hyperglycemia KK-A$^y$ mice

| | | group | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| blood sugar at the 1st day | 0 | 7.85 | 15.3 | 14.7 | 14.8 | 14.9 | 14.7 | 14.5 | 14.5 | 14.2 | 14.1 | 14.9 | 14.8 | 14.8 | 14.4 | 14.8 |
| | 30 min | 7.54 | 15.1 | 11.1 | 9.2 | 9.21 | 6.24 | 11.3 | 9.42 | 9.32 | 6.24 | 9.85 | 7.25 | 5.94 | 7.32 | 5.12 |
| 2st day | Body weight (g) | 27.8 | 30.2 | 30.6 | 30.7 | 30.3 | 30.5 | 30.1 | 30.3 | 30.3 | 30.4 | 30.7 | 30.5 | 30.4 | 30.2 | 30.1 |
| | blood sugar | 7.56 | 15.23 | 17.3 | 10.1 | 13.98 | 13.2 | 17.23 | 10.2 | 13.12 | 13.25 | 13.05 | 12.2 | 12.08 | 12.3 | 12.2 |
| 5st day | Body weight (g) | 27.8 | 30.5 | 30.8 | 30.8 | 30.2 | 30.3 | 30.23 | 30.43 | 30.51 | 30.36 | 30.53 | 30.8 | 30.8 | 30.4 | 30.5 |
| | blood sugar | 9.59 | 15.9 | 14.1 | 10.8 | 13.5 | 12.9 | 14.1 | 10.8 | 13.5 | 12.5 | 13.9 | 11.1 | 11 | 11.4 | 11.2 |
| 8st day | Body weight (g) | 28.4 | 31 | 30.5 | 30.9 | 30.3 | 30.2 | 30.6 | 30.8 | 30.4 | 30.2 | 30.8 | 31.1 | 30.4 | 31.4 | 30.5 |
| | blood sugar | 9.97 | 15.9 | 13.8 | 7.1 | 14.1 | 12.8 | 13.8 | 7.12 | 14.1 | 12.8 | 13.8 | 8.5 | 7.14 | 8.1 | 7.3 |
| 11st day | Body weight (g) | 29 | 32.1 | 30.5 | 31.2 | 31.5 | 30.1 | 30.8 | 31.3 | 31.4 | 30.5 | 30.6 | 31 | 30.7 | 31.4 | 30.8 |
| | blood sugar | 9.31 | 16.1 | 15.1 | 8.2 | 14.2 | 12.8 | 15.3 | 8.21 | 14.3 | 12.9 | 13.5 | 8.2 | 7.95 | 8.4 | 7.5 |
| 14st day | Body weight (g) | 29.6 | 33.4 | 31.2 | 31.5 | 32.5 | 30.4 | 31.25 | 31.76 | 32.56 | 30.4 | 30.7 | 31.8 | 31 | 30.3 | 31.4 |
| | blood sugar | 9.51 | 16.5 | 12.3 | 8.2 | 13.9 | 12.5 | 12.4 | 8.3 | 13.2 | 12.5 | 13.7 | 8.2 | 7.04 | 8.4 | 8.2 |
| 17st day | Body weight (g) | 30.2 | 33.9 | 31.8 | 31.5 | 32.1 | 30 | 31.4 | 31.5 | 32.6 | 30.7 | 30.8 | 30.5 | 30.9 | 30.5 | 30.4 |
| | blood sugar | 10.2 | 16.7 | 13.1 | 8.2 | 14.5 | 12.3 | 13.1 | 8.2 | 14.5 | 12.5 | 13.5 | 8.5 | 7.35 | 8.6 | 7.7 |
| 20st day | Body weight (g) | 31.5 | 35 | 32.1 | 31.6 | 32.5 | 30.1 | 32.1 | 31.3 | 32.2 | 30.2 | 30.5 | 30.5 | 30.7 | 30.4 | 30.8 |
| | blood sugar | 10.25 | 16.9 | 12.8 | 10.1 | 14.59 | 12.5 | 12.43 | 10.23 | 14.12 | 12.45 | 13.24 | 8.1 | 7.98 | 8.2 | 7.5 |

TABLE 11

Effects of compounds S13 and S28 on glucose tolerance of hyperglycemia KK-A$^y$ mice

| group | 0 min | 30 min | 60 min | 120 min |
|---|---|---|---|---|
| 1 | 10.2 | 10.9 | 10.2 | 8.8 |
| 2 | 9.35 | 26.21## | 25.12## | 22.00## |
| 3 | 9.6 | 12.5** | 10.2** | 8.2** |
| 4 | 6.9* | 9.1** | 9.1** | 5.2** |
| 5 | 7.96 | 16.95** | 13.20** | 10.93** |
| 6 | 6.90* | 14.00** | 12.45** | 11.90** |
| 7 | 9.5 | 11.3** | 10.5** | 8.3** |
| 8 | 6.8** | 9.3** | 9.3** | 5.1** |
| 9 | 7.6* | 16.9 | 13.2 | 10.9** | lipemia, which is probably achieved by enhancing the activity of SOD, and the results are shown in table 12.

TABLE 12

Effects of compounds S13 and S28 on blood lipid and liver function of hyperglycemia KK-A$^y$ mice

| group | TC mg/dL | LDL-C mg/dL | HDL-C mg/dL | TG mg/dL | SOD U/L | ALT U/L | AST U/L |
|---|---|---|---|---|---|---|---|
| 1 | 131 | 53 | 22.3 | 310 | 5.0 | 60.2 | 46.1 |
| 2 | 199## | 79## | 24.1 | 628## | 3.2## | 92.4## | 134.7## |
| 3 | 132** | 64* | 22.4 | 328** | 5.01** | 72.1** | 56.2** |
| 4 | 134** | 64** | 22.4 | 310** | 4.24* | 72.8** | 63.5** |

TABLE 12-continued

Effects of compounds S13 and S28 on blood lipid and liver function of hyperglycemia KK-A$^y$ mice

| group | TC mg/dL | LDL-C mg/dL | HDL-C mg/dL | TG mg/dL | SOD U/L | ALT U/L | AST U/L |
|---|---|---|---|---|---|---|---|
| 5 | 131** | 64** | 22.5 | 327** | 4.11** | 67.1** | 60.8** |
| 6 | 125** | 53** | 22.1 | 310** | 4.52** | 61.2** | 60.5** |
| 7 | 134** | 64** | 22.1 | 325** | 5.12** | 72.5** | 56.5** |
| 8 | 134** | 69* | 22.3 | 312** | 4.25* | 71.2** | 63.6** |
| 9 | 135** | 69* | 22.5 | 331** | 4.12** | 62.5** | 60.6** |
| 10 | 123** | 54** | 22.4 | 312** | 4.34* | 61.5** | 60.6** |
| 11 | 176* | 72 | 23.1 | 578 | 3.7 | 89.6 | 137.5 |
| 12 | 166* | 65** | 22.7 | 450** | 3.8 | 80.5 | 110.1 |
| 13 | 152** | 69* | 22.5 | 442** | 4.12* | 77.4** | 97.4** |
| 14 | 166* | 63* | 22.4 | 463* | 3.5 | 85.4 | 100.6* |
| 15 | 158** | 71 | 22.7 | 412** | 4.1* | 76.1* | 87.7** |

Comparing with normal group, #P < 0.05, ##P < 0.01;
comparing with model group, *P < 0.05, **P < 0.01.

It has shown in FIG. 1 that there are different sizes of fat vacuole in hepatocyte of mice of model group and hepatic adipose infiltration is formed, while fat vacuole in hepatocyte of mice of compounds S13 and S28 group almost disappear, which are consistent with the results obtained from the examination of liver by the unaided eye when dissected and the observation of HE staining of histopathological sections thereof. It is indicated that different dose groups of compounds S13 and S28 can effectively treat the nonalcoholic fatty liver disease caused by diabetes.

Example 13, Effects of Compounds S13 and S28 on Non-Alcohol Fatty Liver Disease

Materials: accurately weigh the 2 compounds S13 and S28 prepared in example 1, and then add 0.5% CMC-Na to make the solution of 5 mg/ml used for activity test. 60 Male SPF level Wister rats with the body weight of 180-220 g are purchased from Beijing Vital River Laboratory Animal Technology Co., Ltd. Experiments are carried out after adapting to the environment (T=20-24° C., constant humidity: 50-60%, 12 hours light exposure (8:00-20:00), soundproof, free feeding and drinking) for 1 week. Serum total cholesterol kit (batch number 20131112), low density lipoprotein LDL-C kit (batch number 20140114), high density lipoprotein HDL-C kit (batch number 20140413), triglyceride TG kit (batch number 20131226) and glutamic-pyruvic transaminase ALT kit (batch number 20131006) are purchased from Nanjing Jiancheng Bioengineering Institute.

Methods: male SPF level Wister rats are randomly divided into groups: (1) normal group (2) model control group (3) which is administered by compound S13 with the dose of 10 mg/kg (4) which is administered by compound S13 with the dose of 20 mg/kg (5) which is administered by compound S28 with the dose of 10 mg/kg (15) which is administered by compound S28 with the dose of 20 mg/kg. Each group has 10 mice. The mice of normal group are fed with standard diet, the mice of other groups are fed with choline deficient diet (high-fat diet). Food intake and body weight are detected. Feeding with choline deficient diet are considered as a frequently-used hepatic adipose infiltration modeling method of rodent, which can induce the denaturation of hepatocyte, hepatitis and liver injury, at the same time the increase of blood lipid level can induce the insulin resistance.

After being fed with high-fat diet for 8 weeks, the mice of treated group are given drugs for 4 weeks successively. Model group and normal group are given with equal amounts of 0.5% CMC-Na. After administration of medicine for 4 weeks, the rats are executed under anesthesia, and then hepatic tissue and blood are collected.

Determination Index:
1) Liver index.
2) Contents of serum total cholesterol, low density lipoprotein, high density lipoprotein and triglyceride.
3) Contents of glutamic-pyruvic transaminase.
4) Hepatic tissue section: after the last administration, the rats are executed under anesthesia. Collect the liver on the ice, then quickly fix the liver into formalin and prepare the tissue sections.

The results are shown in table 13. Comparing with the normal group, liver index of model group has increased significantly. Compounds S13 and S28 can effectively decrease the liver index of fatty liver rats. At the same time, TC, LDL-C and TG of model group have increased significantly and HDL-C has decreased significantly, which suggest that obvious dyslipidemia occurs in the present model. Comparing with model group, compounds S13 and S28 can decrease the blood lipid of non alcohol fatty liver mice, improve the liver function and decrease the content of plasma ALT.

TABLE 13

Effects of compounds S13 and S28 on non-alcohol fatty liver disease

| group | Liver index | TC mmol/L | LDL-C mmol/L | HDL-C mmol/L | TG mmol/L | ALT U/L |
|---|---|---|---|---|---|---|
| Normal group | 2.39 | 1.12 | 0.68 | 0.86 | 0.96 | 35.5 |
| Model group | 3.73## | 3.69## | 1.13## | 0.49# | 1.97## | 67.25## |
| S13 (10 mg/kg) | 2.85** | 1.81** | 0.83* | 0.57* | 1.21** | 48.24** |
| S13 (20 mg/kg) | 2.47** | 1.37** | 0.71** | 0.72** | 1.08** | 33.56** |
| S28 (10 mg/kg) | 2.91** | 1.95** | 0.79** | 0.61** | 1.38** | 45.97** |
| S28 (20 mg/kg) | 2.58** | 1.36** | 0.70** | 0.68** | 1.15** | 41.08** |

Comparing with normal group, #P < 0.05, ##P < 0.01;
comparing with model group, *P < 0.05, **P < 0.01.

The liver is examined by the unaided eye when dissected and the HE staining of histopathological sections thereof is observed. It has shown that there are lots of different sizes of fat vacuole in hepatocyte of mice of model group while fat vacuole in hepatocyte of mice of compounds S13 and S28 group almost disappear.

Example 14 Acute Toxicity Test of Mice

Materials: 20 Kunming species mice of 6-8 weeks of 20-22 g are purchased from Beijing Vital River Laboratory Animal Technology Co., Ltd.,
Methods:
1) Preparation of Compounds
Accurately weigh the 2 compounds S13 and S28, and then add 0.5% CMC-Na to make the solution of 0.2 g/ml.
2) Animals Grouping and Administration
After being acclimatized for 3-5 days, the mice are fasted at 18:00 in the day before the experiment, free drinking. The mice are randomly divided into groups of 10 animals in each and given with medicine by intragastric administration, and 0.25 ml of drugs is given to every 10 g weight of mice, i.e. dose 5 g/kg. Mice of control group are given with 0.5% CMC-Na by intragastric administration, and 0.25 ml of solution are given to every 10 g weight of mice.
3) Determination Index
After administration, observe the general status of mice, such as appearance, behavior, response to stimulus, secretion and excretion, and record the time when abnormal phenomena happen. If death occurred, record time and observe the abnormal phenomena by autopsy.

In this test, according to $LD_{50}$ value, intragastric administration toxicity classification of mice and rats are divided into 5 grades: $LD_{50}<1$ mg/kg, extremely toxic; $LD_{50}=1-50$ mg/kg, highly toxic; $LD_{50}=51-500$ mg/kg, moderate toxicity; $LD_{50}=501-5000$ mg/kg, low toxicity; $LD_{50}>5000$ mg/kg actually non-toxic.

Results

No obvious abnormal phenomena are found after administration and the body weight of mice in S28 administration group drop slightly. The mice are executed by cervical dislocation, and no obvious abnormal phenomena are found by autopsy.

$LD_{50}$ of the compounds S13 and S28 are greater than 5000 mg/kg, and no obvious abnormal phenomena are found by autopsy, which suggest that compounds S13 and S28 are actually non-toxic.

The invention claimed is:

1. An aromatic farnesyl compound of formula (I) or pharmaceutically-acceptable salt thereof:

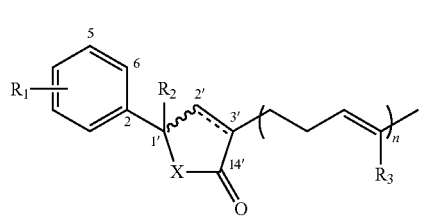

formula (I)

wherein, $R_1$ is selected from H, $C_1$-$C_5$ alkyl group —$NO_2$, F, Cl, Br, ester group, and acylamino group the number of $R_1$ is 1, 2 or 3; configuration of 1' is selected from R type and S type; $R_2$ is H; X is O; the bond between 2' and 3' is a double bond; n=1, 2 or 3; and $R_3$ is $CH_3$.

2. A compound or its pharmaceutically-acceptable salt selected from the group consisting of:

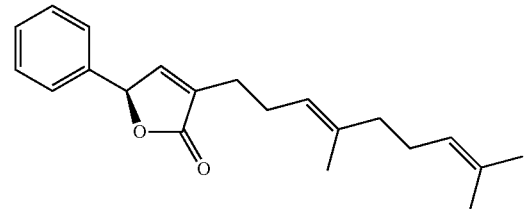

S1

S2

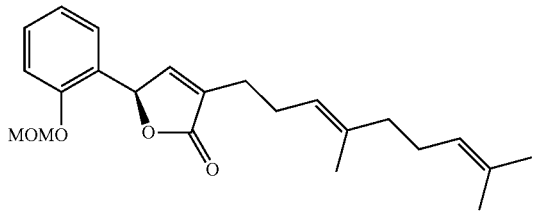

S3

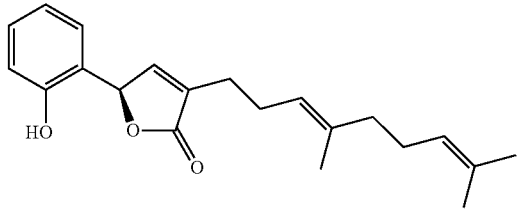

S4

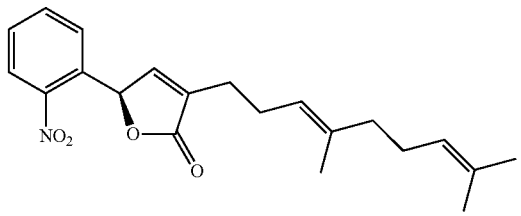

S5

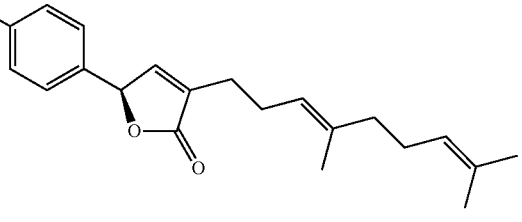

S6

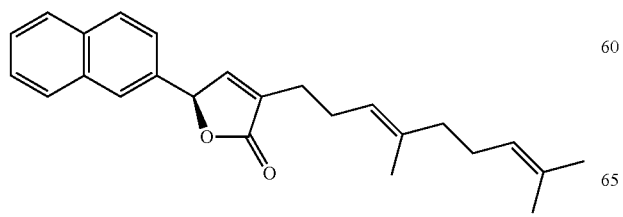

S7

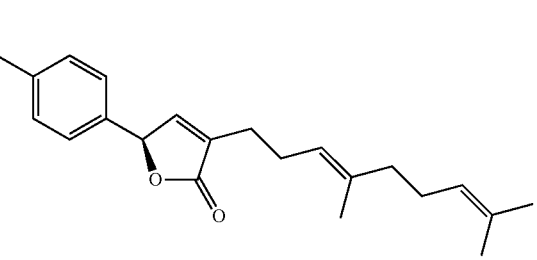

S8

S9
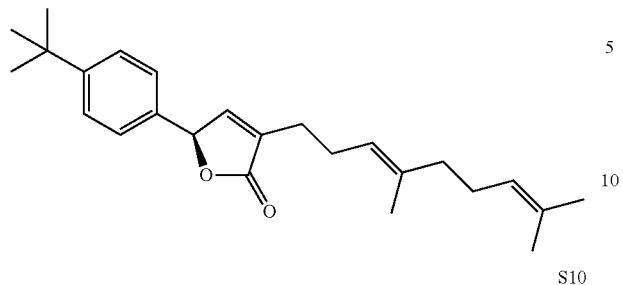
S10
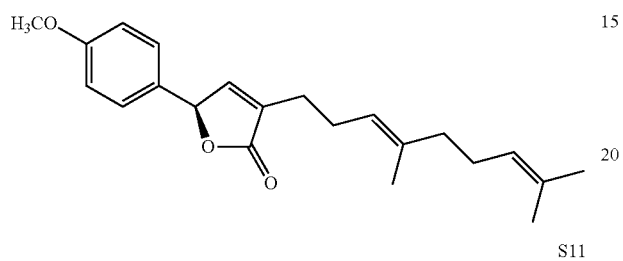
S11
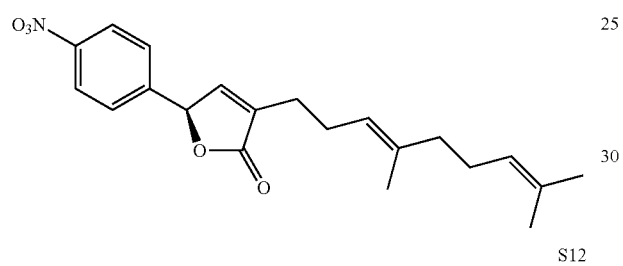
S12
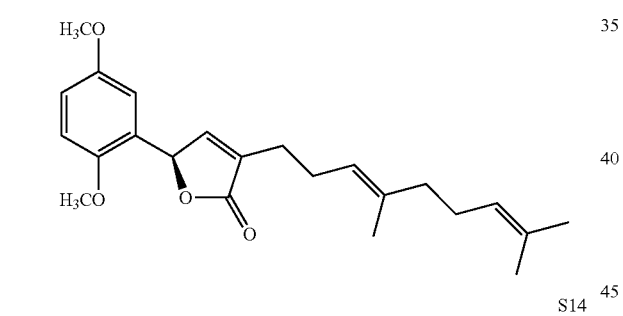
S14
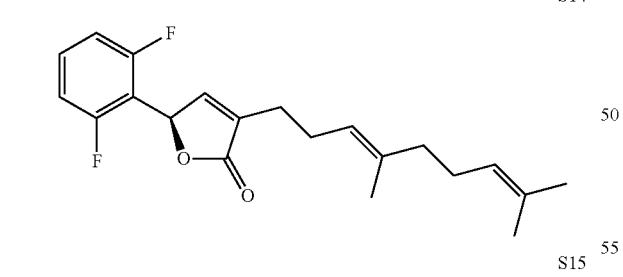
S15
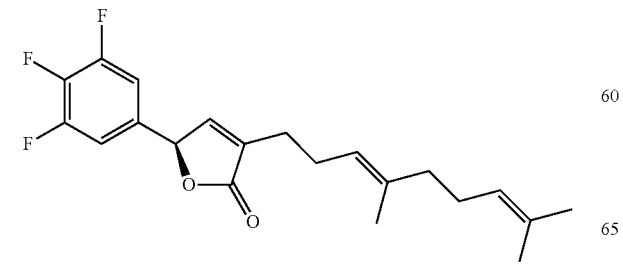
S16
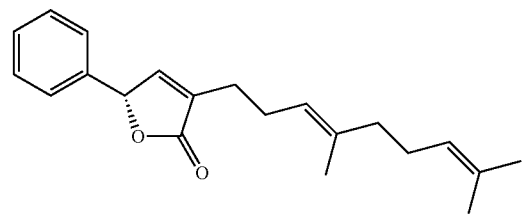
S17
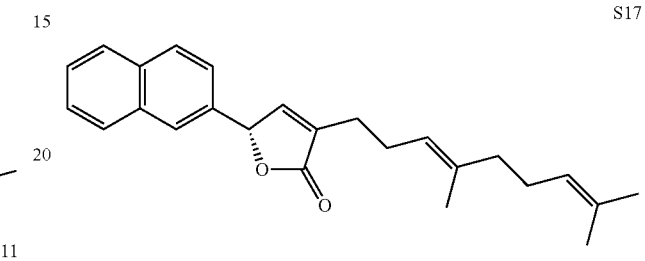
S18
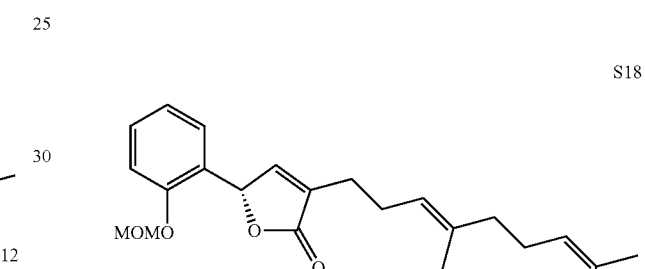
S19
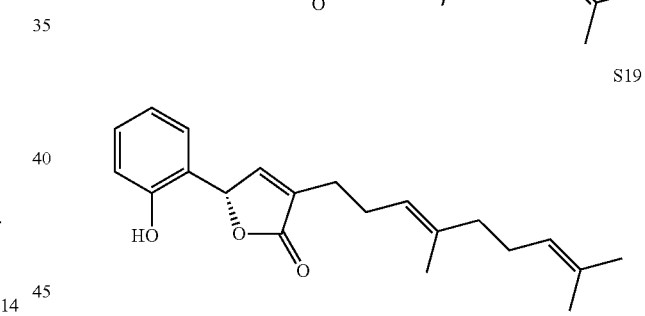
S20
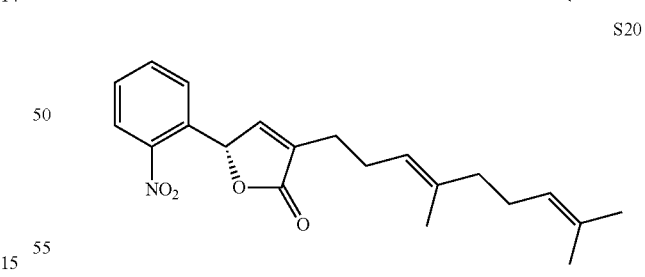
S21
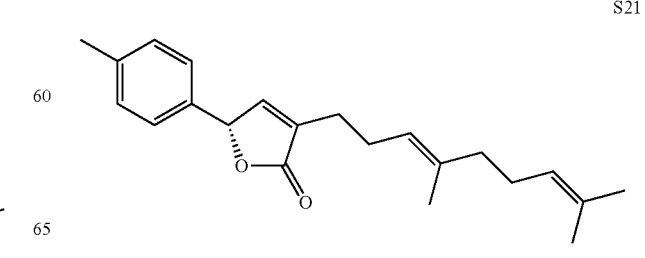

S22 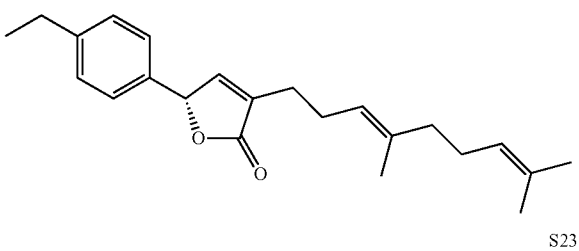

S23 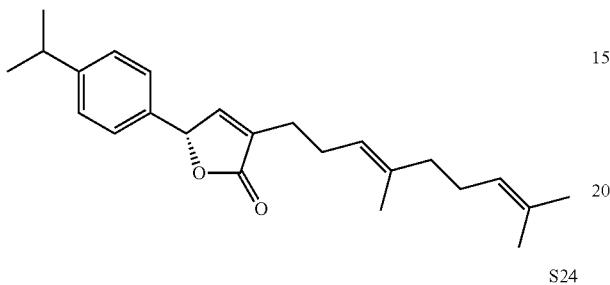

S24 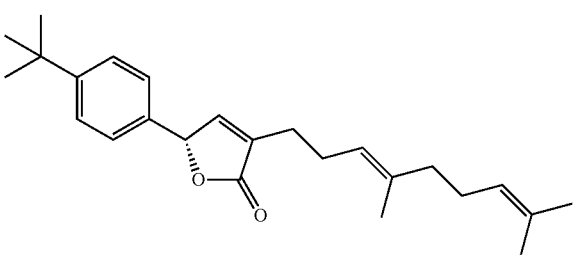

S25 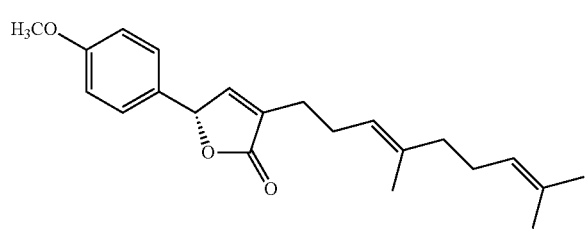

S26 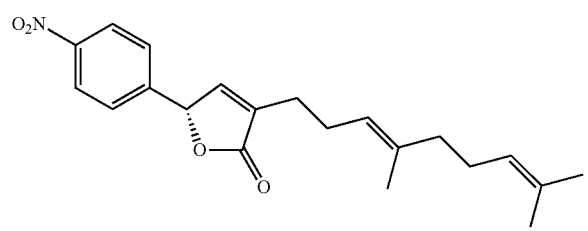

S27 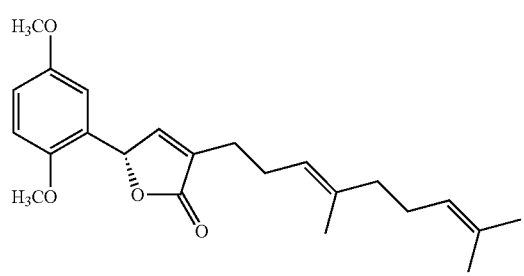

S28 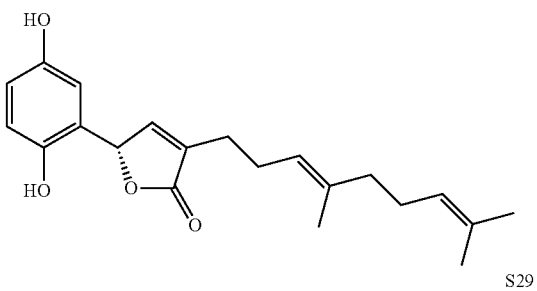

S29 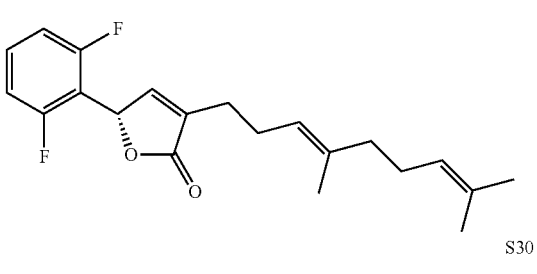

S30

.

3. A method for treating a condition in a subject in need thereof, comprising administering to the subject a composition comprising a compound of claim 2, wherein the condition is selected from the group consisting of diabetes type II; hyperlipidemia; hyperglycaemia; diabetic retinopathy; diabetic foot; non-alcohol fatty liver disease; and combinations thereof.

4. A composition comprising metformin and at least one aromatic farnesyl compound or pharmaceutically-acceptable salt thereof according to claim 1.

5. The method according to claim 3, wherein the composition is an injection, tablet, granule, powder, pill, capsule, oral liquid, ointment, cream or spray.

6. The composition according to claim 4, wherein the composition is a food or functional health product selected from the group consisting of oral liquids, teas, tablets, capsules, drinks and effervescent tablets.

7. The method according to claim 3, wherein the composition further includes one or more pharmaceutically-acceptable excipients.

8. The method according to claim 7, wherein said excipients are selected from the group consisting of diluents, fillers, adhesives, wetting agents, disintegrating agents, absorption enhancers, surfactants, adsorption carriers, lubricants and sustained-release materials.

9. The method according to claim 3, wherein the administration is by oral administration, gastrointestinal administration, injection, spray, or physical or chemical mediated administration.

10. A composition comprising metformin and at least one compound according to claim 2.

11. A method for treating a condition in a subject in need thereof, comprising administering to the subject a composition comprising a compound of claim 1, herein the condition is selected from the group consisting of diabetes type II, hyperlipidemia, hyperglycemia, diabetic retinopathy, diabetic foot, non-alcohol fatty liver disease, and combinations thereof.

12. The method according to claim 11, wherein the composition is an injection, tablet, granule, powder, pill, capsule, oral liquid, ointment, cream or spray.

13. The composition according to claim 10, wherein the composition is a food or functional health product selected from the group consisting of oral liquids, teas, tablets, capsules, drinks and effervescent tablets.

14. The method according to claim 11, wherein the composition further includes one or more pharmaceutically-acceptable excipients.

15. The method according to claim 14, wherein said excipients are selected from the group consisting of diluents, fillers, adhesives, wetting agents, disintegrating agents, absorption enhancers, surfactants, adsorption carriers, lubricants and sustained-release materials.

16. The method according to claim 11, wherein the administration is by oral administration, gastrointestinal administration, injection, spray, or physical or chemical mediated administration.

* * * * *